United States Patent [19]
Fuchs et al.

[11] Patent Number: 5,948,231
[45] Date of Patent: Sep. 7, 1999

[54] COMPOSITIONS, METHODS AND APPARATUS FOR ULTRAFAST ELECTROSEPARATION ANALYSIS

[75] Inventors: Martin Fuchs, Uxbridge; Wassim A. Nashabeh, Chestnut Hill; Dieter R. Schmalzing, Boston, all of Mass.

[73] Assignee: PerSeptive Biosystems, Inc., Framingham, Mass.

[21] Appl. No.: 08/853,031

[22] Filed: May 8, 1997

Related U.S. Application Data

[63] Continuation of application No. 08/425,828, Apr. 20, 1995, Pat. No. 5,630,924.

[51] Int. Cl.$^6$ .................................................. G01N 27/26
[52] U.S. Cl. ........................... 204/601; 204/603; 204/604
[58] Field of Search ..................................... 204/451, 452, 204/453, 601, 603, 604

[56] References Cited

U.S. PATENT DOCUMENTS

| | | | |
|---|---|---|---|
| 4,329,213 | 5/1982 | Elwing | 204/180 G |
| 4,486,530 | 12/1984 | David et al. | |
| 5,120,413 | 6/1992 | Chen et al. | |
| 5,122,248 | 6/1992 | Karger et al. | 204/182.8 |
| 5,137,609 | 8/1992 | Maman et al. | 204/180.1 |
| 5,348,633 | 9/1994 | Karger et al. | |

FOREIGN PATENT DOCUMENTS

WO 93/20236  10/1993  WIPO.

OTHER PUBLICATIONS

Nielsen et al. (1991), "Separation of Antibody–Antigen Complexes By Capillary Zone Electrophoresis, Isoelectric Focusing and High–Performance Size–Exclusion Chromatography," 539 *J. Chromatography* 177–185.

Schultz et al. (1993), "Rapid Immunoassays Using Capillary Electrophoresis With Fluorescence Detection," 65 *Anal. Chem.* 3161–3165.

Shimura et al. (1994), "Affinity Probe Capillary Electrophoresis: Analysis of Recombinant Human Growth Hormone With A Fluorescent Labeled Antibody Fragment," 55 *Anal. Chem.* 9–15.

Chen et al. (1994), "Characterization of Proteins By Capillary Electrophoresis in Fused–Silica Columns: Review on Serum Protein Analysis and Application to Immunoassays," 15 *Electrophoresis* 13–21.

Chen et al. (1994), "Feasibility Studies for Simultaneous Immunochemical Multianalyte Drug Assay by Capillary Electrophoresis with Laser–Induced Fluorescence," 40 *Clin. Chem.* 9:1819–1822.

Raymond et al. (1994), "Continuous Sample Pretreatment Using A Free–Flow Electrophoresis Device Integrated Onto A Silicon Chip," 66 *Anal. Chem.* 2858–2865.

Reif et al. (1994), "Fluorescein Isothiocyanate–Labeled Protein G As An Affinity Ligand In Affinity/Immunocapillary Electrophoresis With Fluorescence Detection," 66 *Anal. Chem.* 4027–4033.

(List continued on next page.)

*Primary Examiner*—David A. Redding
*Attorney, Agent, or Firm*—Testa, Hurwitz & Thibeault LLP

[57] ABSTRACT

Compositions, methods, and apparatus for performing ultrafast binding assays by capillary electrophoresis or other electroseparation techniques are disclosed. In one embodiment, a first binding partner carries a detectable label and a second binding partner is modified to be highly charged. When used in combination with a sample containing an analyte with which both binding partners can interact and bind thereto, a three-membered complex is formed. The electrophoretic mobility difference between the unbound and complex-bound forms of labeled first binding partner is such that electroseparation and subsequent detection of an analyte can be accomplished. The compositions, methods, and apparatus disclosed herein also permit quantitative determination of the concentration of an analyte in a sample.

23 Claims, 7 Drawing Sheets

OTHER PUBLICATIONS

Evangelista et al. (1995), "Simultaneous Multianalyte Immunoassay of Drugs of Abuse by CE," 14 *Amer. Clin. Lab.* 2:27–28.

Schmalzing et al. (1995), "Rapid Capillary Electrophoresis Based Immunoassays," Abstract, AACC Oak Ridge Conference, to be presented Apr. 28, 1995.

Schmalzing et al. (1995), "Rapid Capillary Electrophoresis Based Immunoassays," Abstract of presentation given at 1995 AACC Oak Ridge Conference, San Antonio, Texas, Apr. 28, 1995.

Egholm et al. (1993), "PNA Hybridizes to Complementary Oligonucleotides Obeying the Watson–Crick Hydrogen–Bonding Rules," 365 *Nature* 566–568.

Chen et al. (1994), "Characterization of Charge–Modified and Fluorescein–Labeled Antibody by Capillary Electrophoresis Using Laser–Induced Fluorescence," 680 *J. Chromatography* 2:419–423.

COMPOSITIONS, METHODS AND APPARATUS FOR ULTRAFAST ELECTROSEPARATION ANALYSIS

This is a continuation of application Ser. No. 08/425,828 filed on Apr. 20, 1995, now U.S. Pat. No. 5,630,924.

FIELD OF THE INVENTION

The present invention relates generally to the field of binding assays and more specifically to methods and compositions for performing binding assays using electroseparation techniques such as electrophoresis.

BACKGROUND OF THE INVENTION

Electrophoresis is a well-established technique for the separation and analysis of mixtures. Electrophoresis involves the migration and separation of molecules in an electric field based on differences in mobility. Many different forms of electrophoresis have been developed to permit the separation of different classes of compounds. These forms include free zone electrophoresis, gel electrophoresis, isoelectric focusing, and isotachophoresis. These techniques can be performed in tubes or channels of micrometer cross-sectional dimensions in what is referred to as capillary electrophoresis (CE). Capillary electrophoresis offers advantages over larger scale systems with regard to assay time and electrophoretic resolution because high electrical field strengths can be used and the technique is readily automatable.

CE is a powerful separation technique and can be used, for example, to separate an antibody-antigen complex from either the unbound form of the antigen or the antibody, thereafter permitting quantitation. when the interaction between analyte and binding partner, e.g., antibody and antigen, is highly specific, the combination of this highly specific reaction with conjugation techniques for attaching a detectable moiety to binding partners makes it possible to use a variety of assay techniques to detect analytes in complex biological samples such as body fluids. For example, U.S. Pat. No. 4,486,530 discloses use of monoclonal antibodies and detectable moieties to determine the presence and/or concentration of IgE in a sample. In general, CE assays have more favorable characteristics such as shorter assay time, less sample volume requirements, low reagent usage, and potentially enhanced sensitivity. See e.g., Reif et al., *Analytical Chemistry* 66:4027–4033 (1994).

One of the key factors in successfully employing conventional CE or other.electroseparation techniques for immunoassays is the ability to electrophoretically separate unbound and bound forms of antibody. Despite the high resolution power of electroseparation techniques, however, this is not a readily or reliably achievable requisite. A major reason for this is that the antigen, the antibody, or both may exhibit significant heterogeneity due to the presence of variants, isoforms, differences in glycosylation, etc. This means that both the unbound and the complexed form of the antibody migrate non-uniformly, thus producing broad poorly-defined distributions upon electroseparation analysis rather than sharply discernible peaks as desired. Consequently, detection and/or quantitation of unbound versus bound species is difficult and/or unreliable. Thus, for certain analytes, especially large biomolecules, conventional electroseparation methods may not offer significant advantages for clinically useful diagnostic immunoassay applications.

Electroseparation has also been used to analyze nucleic acid analytes as disclosed in WO 93 20236, entitled "Probe Composition and Method." The probes described therein contain nucleic acid analytes and a polynucleotide binding partner attached thereto. The polynucleotide component of the probes is attached to a detectable label as well as a size and/or charge modifier to assist in the electrophoretic fractionation of the individual polynucleotide component upon its release from the probe. Analysis of nucleic acid analytes is accomplished indirectly by correlating the presence/absence of an individual released polynucleotide with the presence/absence of a particular nucleic acid analyte.

Some practitioners have also tailored the electrophoretic mobility of a labeled antibody by attaching charged groups to the same labeled molecule. See, e.g., Chen and Evangelista, *Clinical Chemistry* 40:1819–1822 (1994); Chen and Sternberg, *Electrophoresis* 15:13–21 (1994). On the one hand, this results in the mobility of labeled antibody being different from that of the corresponding unlabeled antibody. On the other hand, however, tailoring the charge characteristics of the labeled antibody is not ideal because the ultimate objective of the assay is to separate the two labeled species formed in a typical binding assay of the sort disclosed in the above-mentioned references, i.e., labeled antibody-antigen complex and unbound labeled antibody. According to the methodologies set forth in the above-mentioned references, both such species will be influenced by the charge tailoring, thereby undermining efforts to differentiate between labeled species. Additionally, while the above-described references demonstrate some success using a single antibody having dual modifications, i.e., having both a detectable moiety and a charged moiety attached thereto, the analytes detected are small, low-molecular weight analytes (morphine, PCP, digoxin), with the assay performed in a competitive format, which are typically more conducive to CE analysis than more complex biological macromolecules. See also Evangelista et al., *American Clinical Laboratory* 14(2):27–28 (1985).

SUMMARY OF THE INVENTION

Accordingly, the present invention is directed to an electroseparation method which substantially obviates one or more of the problems due to limitations in the prior art. These and other objects, along with advantages and features of the invention disclosed herein, will be apparent from the description, drawings and claims that follow.

In one aspect, the present invention provides a method for electroseparation analysis of a mixture involving the step of electrically separating in a channel a mixture containing: (1) a sample; (2) a first binding partner which binds to a first binding site on an analyte; and, (3) a second binding partner which binds to a second binding site on the analyte, whereby first and second binding partners bind to analyte, if present in the sample, to form a three-membered complex which is electrically separable from unbound first binding partner. The method further provides that a detectable moiety is attached to the first binding partner and that a charge-modifying moiety is attached to the second binding partner such that the three-membered complex exhibits an electrophoretic mobility different from that of unbound first binding partner upon exposure to an electrical potential.

In another embodiment, the claimed method for detecting the absence, presence or concentration of an analyte in a sample involves: combining a first binding partner which binds to a first binding site on an analyte and a second binding partner which binds to a second binding site on the analyte with a sample to produce a mixture, so that the analyte, if present, will form a three-membered complex comprising analyte, first binding partner and second binding partner; disposing the mixture within an electroseparation channel containing an electrically-conductive medium; applying an electrical potential to the channel to separate the three-membered complex, if present, from unbound first binding partner; and, detecting the complex formed.

In one embodiment of the instant invention, the method of detecting the absence, presence or concentration of an analyte in a sample involves combining the first and second binding partners with a sample within the electroseparation channel. In this embodiment, it is contemplated that the three-membered complex forms within the channel, possibly to facilitate complex formation and reduce assay time. In another embodiment, the instant invention provides a method wherein a first or second binding partner is immobilized within the electroseparation channel. In this instance, the immobilized partner is released prior to application of the electrical potential.

In yet another embodiment, the method of the instant invention provides an electroseparation channel characterized by a first zone containing first binding partner and a second zone containing second binding partner, wherein a sample is disposed within the channel and contacted with both zones thereby permitting formation of a three-membered complex containing first binding partner, second binding partner, and analyte if present in the sample. Electroseparation and detection of the three-membered complex is achieved as described herein.

The instant invention contemplates detection of at least one three-membered complex per species of analyte in a sample, and further contemplates multi-analyte electroseparation analysis for detection of a plurality of analytes in a single sample, wherein formation of a three-membered complex is indicative of the presence of a particular analyte in the sample.

In another aspect, the invention features a composition for the detection of an analyte composed of (1) an analyte; (2) a first binding partner which binds to a first binding site on said analyte and which has a detectable moiety attached thereto; and, (3) a second binding partner which binds to a second binding site on the analyte which has a charge-modifying moiety attached thereto. It is contemplated that the second binding site is distinct from said first binding site such that a three-membered complex forms wherein the first and second binding partners are bound to said analyte, and such that the three-membered complex exhibits an electrophoretic mobility different from that of unbound first binding partner.

The present invention further provides a composition wherein the first binding site on said analyte comprises a first binding partner recognition site to which the first binding partner binds and which is not recognized by said second binding partner. Additionally, the present invention also provides a composition wherein the first binding partner comprises a first analyte-recognition site distinct from a linkage site at which said first binding partner and a detectable moiety are linked. Similarly, the present invention provides a composition wherein the second binding site on the analyte comprises a second binding partner recognition site to which the second binding partner binds and which is not recognized by said first binding partner. The composition of the present invention further features a second binding partner having a second analyte-recognition site distinct from a linkage site at which the second binding partner and a charge-modifying moiety are linked. In other embodiments, the present invention provides a composition in which the first binding partner and/or the second binding partner are derived from a monovalent antibody or from an F(ab') or an F(ab')$_2$ antibody fragment.

In another aspect, the invention features an apparatus for the detection of an analyte characterized by: an electroseparation channel having an electrically-conductive medium disposed within; an injection zone; a sample disposed within the injection zone, the sample containing an analyte, a first binding partner which binds to a first binding site on the analyte, and a second binding partner which binds to a second binding site on the analyte; and, a source of voltage for imposing an electric potential across the channel. The present invention provides that a detectable moiety is attached to the first binding partner and a charge-modifying moiety is attached to the second binding partner. The present invention further provides that the second binding site is distinct from the first binding site such that the analyte, the first binding partner, and the second binding partner form a three-membered complex.

The present invention also features an apparatus in which the electrophoretic mobility of said three-membered complex differs from that of said unbound first binding partner. In certain embodiments of the present invention, activation of the electric potential results in the three-membered complex and unbound first binding partner resolving into two opposite moving zones as disclosed herein.

In certain embodiments of the apparatus of the present invention, electroseparation of the analyte-containing complex from the binding partners is accomplished by electrophoresis. As disclosed herein, electroseparation is currently preferably accomplished by free zone or free flow electrophoresis.

In one embodiment of the instant invention, the apparatus is characterized by an electroseparation channel which is engraved, etched or otherwise disposed within a suitable substrate. It is contemplated that the electroseparation channel is a flow-through passage of suitable depth, width, and length. In certain embodiments, the electroseparation channel is a linear passage through said substrate. In certain other embodiments, the electroseparation channel is branched.

It is further contemplated that the apparatus of the instant invention has an electroseparation channel derived from a solid substrate as disclosed herein microfabricated to define a channel. In another embodiment, the instant invention provides an apparatus having a multiplicity of microfabricated channels disposed within said substrate. In some other embodiments, the apparatus has a single channel. In yet other embodiments, the instant invention provides an apparatus for the detection of an analyte wherein the electroseparation channel is a capillary, preferably less than about 500$\mu$ in diameter. The capillary can be chemically functionalized as disclosed herein for optimal detection of an analyte using the compositions and methods of the instant invention.

In another embodiment, the invention provides an apparatus for the detection of an analyte in a sample having a detector means for detecting said analyte. The invention contemplates a detector means whereby the three-membered complex is indicative of the presence of analyte in the sample. The invention further contemplates a detector means for quantitatively determining the amount of analyte in a sample. In the instance of these embodiments, the present invention contemplates that quantitative determination of the formation of three-membered complex is indicative of the concentration of analyte in said sample. The present invention contemplates a variety of detector means as disclosed herein.

In yet another embodiment, the present invention features an electroseparation apparatus for the detection of an analyte in a sample, having an electroseparation channel; a means for disposing within the channel a mixture of analyte-containing sample, a first binding partner which binds to a first binding site on the analyte, and a second binding partner which binds to a second binding site on the analyte, and, a three-membered complex wherein the complex contains analyte, first binding partner, and second binding partner; and, a source of voltage for imposing an electrical potential across said channel. Means for disposing the mixture includes mechanical delivery means as well as automated fluid flow means as disclosed herein.

In another aspect, the present invention provides a kit for electroseparation analysis of an analyte in a sample containing: an electroseparation apparatus comprising a channel; a detectable moiety for attachment to a first binding moiety, said first binding moiety competent to bind to a first binding site on an analyte in a sample; and, a charge-modifying moiety for attachment to a second binding moiety, said second binding moiety competent to bind to a second binding site on said analyte in said sample. In one embodiment, the kit further contains attachment reagents with which said detectable moiety and said charge-modifying moiety can be attached to said first and second binding moieties, respectively, to form a first binding partner and a second binding partner, respectively, said first binding partner and said second binding partner being competent to bind to said analyte, if present in said sample, thereby forming a three-membered complex which exhibits an electrophoretic mobility different from that of unbound first binding partner during electroseparation analysis. In certain embodiments, the present invention provides a kit wherein the electroseparation channel is a capillary.

In yet another embodiment, the present invention provides a kit for electroseparation analysis of an analyte in a sample comprising: a first binding partner which binds to a first binding site on an analyte, said first binding partner comprising a detectable moiety; and, a second binding partner which binds to a second binding site on said analyte, said second binding partner comprising a charge-modifying moiety. The invention further provides that electroseparation analysis utilizing such kits results in the first and second binding partners forming a three-membered complex with the analyte, when present, thereby permitting detection of complexed analyte by electroseparation.

The compositions, methods and apparatus for ultrafast electroseparation analysis of the instant invention solve problems encountered in conventional electrophoretic binding assays. For example, the instant invention provides the skilled practitioner with the technical know-how and means to tailor specifically the mobility of an analyte-containing complex without affecting the mobility of the unbound form of binding partner labeled with a detectable moiety. This has several advantages. First, it simplifies assay development. Because the mobility of the complex is now markedly different from that of the unbound binding partner labeled with a detectable moiety, it is no longer necessary to carefully optimize separation conditions to achieve reliable separation of unbound and bound binding partner. Using the compositions, methods, and/or apparatus of the instant invention, an assay can be rapidly developed for any analyte, e.g., antigen, for which two binding partners, e.g., antibodies, that recognize separate sites on the analyte, are available. Matched pairs of antibodies are already used for enzyme-linked immunosorbent assays (ELISA) and other types of sandwich assays, and hence are readily commercially available for many analytes of clinical significance. Moreover, heterogeneity of an antibody binding partner and/or an antigen analyte now has minimal effect on the ability to separate bound and unbound detectably-labeled antibody.

Another advantage realized by the instant invention is that separation time can be dramatically reduced as the mobility difference between unbound and bound components is increased. In the extreme, it is possible to achieve assay conditions in which the unbound and complexed forms have mobility of opposite sign. This means that sufficient separation is achieved at the moment the injection zone has resolved into two opposite moving zones containing unbound and complexed analyte.

As described above, the method of the instant invention features use of two different binding partners, e.g., antibodies, to perform both the detecting and mobility-tailoring functions. Certain embodiments utilize antibody binding partners in the form of a monovalent antibody fragment (Fab or Fab') to minimize agglomeration and enhance sensitivity. As mentioned above, the antibodies recognize distinct sites on the antigen so that both can bind non-competitively to the antigen. In a particular embodiment, one antibody is labeled with a detectable label and the other is modified to be strongly charged. As disclosed herein, the charge modification can be accomplished by various chemical means, such as the attachment of a polynucleotide or a polypeptide such as polylysine or polyglutamic acid to the antibody using well established chemistries. For example, one approach is to produce Fab' fragments followed by attachment of the charge conferring group at a thiol(s) group using an art-recognized thiol reactive chemistry.

In an exemplary binding assay practiced in accordance with the instant invention, both binding partners, e.g., antibodies or antibody fragments, are combined with a sample and incubated to allow equilibrium to be established. Incubated sample is then injected into a free zone capillary electrophoresis electroseparation channel and an electric field is applied to separate of unbound and bound forms of the antibody labeled with a detectable moiety. Because one of the binding partners, i.e., the charge-modified antibody, contributes only to the mobility of the complex-bound antibody and not the unbound antibody, separation of these species happens quickly. In an extreme case, unbound and bound species migrate in opposite directions such that separation is completed as soon as the trailing edges of the free and bound labeled antibody zones clear the injection zone.

In short, the compositions, methods, and apparatus for detection of an analyte by ultrafast electroseparation analysis disclosed herein are highly desirable and demonstrate the following advantages. First, assay development time can be drastically reduced. Because detectable mobility differences result from practice of the instant invention, the need for careful optimization of separation conditions is less crucial. Second, assays can be performed in significantly shorter times because discernible mobility differences result from practice of the instant invention. Third, detectable enzyme labels can now be used far more readily than previously possible. Because many enzymes suitable for generating a detectable signal in an immunoassay, for example, are large bulky proteins, it has been difficult to obtain sufficient mobility differences between unbound and bound forms of an antibody-enzyme conjugate. In accordance with the instant invention, however, the requisite mobility difference is easily achieved using a charge-modified second binding partner. The present invention now permits the skilled artisan to develop and clinically apply sensitive enzyme amplification assays together with CE and other electroseparation techniques to detect physiological concentrations of clinically-significant analytes.

It is to be understood that both the foregoing general description and the following detailed description are exemplary and explanatory and are intended to provide further explanation of the invention as claimed.

BRIEF DESCRIPTION OF THE DRAWINGS

The accompanying drawings are intended to provide a further understanding of the invention and are incorporated and constitute a part of this specification, illustrate several embodiments of the invention and, together with the description, serve to explain the principles of the invention.

DETAILED DESCRIPTION OF PREFERRED EMBODIMENTS

Figure 1:
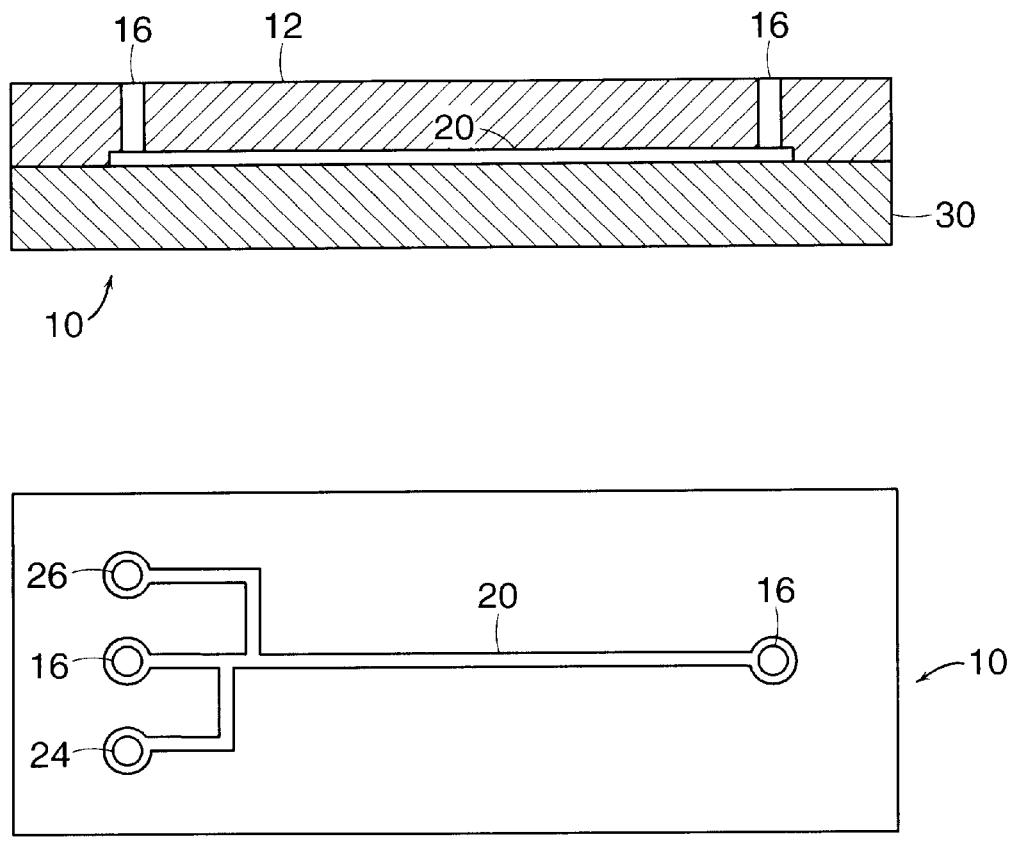
FIG. 1 is a schematic representation of one embodiment of the currently preferred apparatus microfabricated from a solid substrate suitable for electroseparation analysis practiced in accordance with the instant invention.

As will be described below in greater detail, the instant invention relates to compositions, methods, and apparatus for detecting an analyte. Specifically, in certain embodiments, the compositions, methods, and apparatus of the invention relate to separation of components of a mixture by electroseparation to detect an analyte by ultrafast electroseparation analysis.

The compositions comprise a sample, first binding partner, and second binding partner, wherein a first binding partner has a detectable moiety attached thereto, and a second binding partner has a charge modifying moiety attached thereto. These compositions permit separation of unbound first binding partner from bound analyte, if present in the sample, by virtue of differences in electrophoretic mobility, thereby permitting both qualitative and quantitative detection of an analyte in a sample using complex formation as an indication thereof.

The methods of the invention allow the electroseparation of components in a mixture, and further, allow detection of the absence, presence, or concentration of an analyte in a sample using the above-described compositions. Specifically, the methods utilize first and second binding partners such as those described above in combination with a sample to electrically separate analyte-containing complexes from unbound first binding partner. When practiced in accordance with the instant invention, the methods provide for detection of analyte-containing complexes without interference by unbound first binding partner.

The apparatus of this invention comprises an electroseparation channel suitable for practicing the above-described methods utilizing the claimed compositions. In a preferred embodiment, the electroseparation channel is in the form of capillaries and/or solid substrates microfabricated to define a channel or channels.

The subject matter of the present invention further relates to diagnostic reagents and kits for detecting an analyte by ultrafast electroseparation analysis.

As used herein, the term "analyte" is intended to mean any substance susceptible to detection using the instant invention. As will be understood by the skilled practitioner, analytes suitable for use include any moiety able to interact specifically with, and bind with, at least two different binding partners. That is, any analyte which forms a non-transient, i.e., non-intermediary, detectable complex with at least two different binding partners is suitable. Preferred analytes include chemical and biochemical moieties, such as proteins, if peptides, nucleic acids, peptide hormones, non-peptide hormones, drugs of abuse, environmental pollutants, pharmaceuticals, microbial antigens, viral antigens, carbohydrates, polyclonal antibodies, monoclonal antibodies, anti-idiotypic antibodies, antibody fragments, enzyme substrates, enzyme inhibitors, biotin, and receptors. The currently preferred analytes are those of clinical significance, such as hormones, proteins, peptides, microbial antigens, viral antigens, and vitamins. It should be further understood that biochemical or chemical substances which can be rendered amenable to complex formation, i.e., can be manipulated or modified to bind with at least two different binding partners, are considered suitable for use in the claimed invention.

As used herein, the term "sample" is intended to mean any specimen to be analyzed for an analyte of interest. Currently preferred samples include, but are not limited to, any biological or environmental specimen suspected to contain an analyte of interest. Samples suitable for use in the claimed invention can include body fluids including, but not limited to: blood, serum, plasma, urine, cerebrospinal fluid, saliva, sweat, semen, vaginal fluid, amniotic fluid, and ascites fluid. Additionally, samples may include fluids such as, but not limited to, rain water, ocean water, ground water, soil extracts, and sewer water which may be analyzed for environmental pollutants.

As used herein, the term "binding partner" is intended to mean any moiety capable of binding activity. The term binding partner includes, but is not limited to, any biochemical or chemical moiety which has an ability to interact specifically with, and bind with, a corresponding analyte. It will be obvious to those skilled in the art that, in order to practice the claimed invention, the identity of the particular binding partner will be governed by the identity of the particular analyte to be detected. Generally speaking, binding partners suitable for use in the instant invention include, but are not limited to, the following biochemical and chemical moieties: proteins, peptides, nucleic acids, peptide hormones, non-peptide hormones, environmental pollutants, lectins, microbial antigens, viral antigens, carbohydrates, polyclonal antibodies, monoclonal antibodies, anti-idiotypic antibodies, antibody fragments, biosynthetic antibody binding sites, enzymes, avidin, and receptors. Moreover, biochemical or chemical substances which can be rendered amenable to complex formation with a corresponding analyte, i.e., can be manipulated or modified to bind with a particular analyte, are considered suitable for use in the instant invention. Currently preferred binding partners are those suitable for detection of clinically significant analytes.

The "first binding partner," as used herein, comprises at least one detectable moiety and binds specifically to a "first binding site" on the analyte to be detected. The first binding site comprises a first binding partner recognition site to which the first binding partner binds and which is not recognized by the "second binding partner." Moreover, the first binding partner further comprises a first analyte-recognition site distinct from a linkage site at which the first binding partner and a "detectable moiety" are linked.

Similarly, the "second binding partner" comprises at least one "charge modifying moiety" and binds to a second binding site on the analyte to be detected. The second binding partner further comprises a second analyte-recognition site distinct from a linkage site at which the second binding partner and a charge-modifying moiety are linked. It will be understood that the second binding site on the analyte is distinct from the first binding site on the analyte.

As described above, the first and second binding partners may be of the antibody type. Currently, monovalent antibody fragments are preferred. As discussed in detail below, antibody fragments such as the F(ab') or the F(ab')$_2$ fragments which are devoid of the Fc portion of the naturally-occurring antibody molecule are also preferred. Any antibody fragment which demonstrates the requisite binding specificity and demonstrates properties such as diminished agglomeration and steric hindrance, i.e., properties typically exhibited by monovalent antibodies or antibodies lacking the Fc portion, respectively, are suitable binding partners for use in the claimed invention. Identification of other binding partners and equivalents thereof is well within the skill of the ordinary practitioner and would require no more than routine experimentation.

Detectable moieties, as used herein, are moieties suitable for use in the claimed invention including, but not limited to: enzymes, fluorophores, chromophores, radioisotopes, electrochemical moieties, and chemoluminescent moieties. A currently preferred detectable moiety is a fluorescent moiety, for example rhodamine. When practiced in accordance with the instant invention, detectable enzyme labels can now be used far more readily than previously possible. Because many enzymes suitable for generating a detectable signal in an immunoassay, for example, are large bulky proteins, it has been difficult to obtain sufficient mobility differences between unbound and bound forms of an antibody-enzyme conjugate. In accordance with the instant invention, however, the requisite mobility difference is easily achieved using a charge-modified second binding partner. The present invention now permits the skilled artisan to develop and clinically apply sensitive enzyme amplification assays together with CE and other electroseparation techniques to detect physiological concentrations of clinically-significant analytes. Other currently preferred detectable moieties include: fluorescein, cyanine dyes, coumarins, phycoerythrin, phycobiliproteins, dansyl chloride, and Texas Red.

Such moieties can be readily conjugated with any of the above-described first binding partners using art-recognized techniques. It will be understood by the skilled artisan that attachment of such moieties can be accomplished using any means which generates a first binding partner suitable for use in the; instant invention, i.e., the first binding partner retains an ability to bind with the analyte post-conjugation. A currently preferred first binding partner is an F(ab') antibody fragment conjugated with rhodamine, using rhodamine iodoacetamide as described below.

Additionally, the instant invention contemplates a composition comprising a first binding partner having a detectable moiety which is intrinsic, e.g., functional groups on proteins which permit detection of the protein by absorbance of ultraviolet radiation.

As used herein, a "composition" is intended to mean any mixture of, or any combination of, a sample and both first and second binding partners as defined herein suitable for detecting the absence, presence or concentration of an analyte in a sample by electroseparation analysis.

Alternatively, a "composition" means a "three-membered complex" wherein a first and second binding partner are bound to an analyte. By virtue of the above-described detectable moiety attached to the first binding partner, the presence of such a complex is detectable thereby, in turn, indicating the presence of analyte. An advantage of the instant invention relates directly to the discovery that bound second binding partner, as defined herein, permits separation of this three-membered complex from unbound first binding partner sufficient to permit reliable detection of the analyte-containing complex. Because the first binding partner carries a detectable moiety whether in its bound or unbound state, it is necessary to separate the unbound form from the complexed, bound form in order to use complex formation as an indication of the presence of analyte.

Accordingly, as also claimed herein, the second binding partner of the instant invention is linked to at least one "charge-modifying moiety". A charge-modifying moiety is any moiety which imparts to the bound second binding partner the ability to electroseparate analyte-containing complex from unbound first binding partner such that the separation is sufficient to permit detection of the complex. Any such charge-modifying moiety is suitable for use in the instant invention. A charge-modifying moiety suitable for use in the instant invention can impart a negative charge or a positive charge. The skilled artisan would be able to determine the identity of a suitable moiety by routine experimentation.

With respect to all the above-described embodiments of the present invention, the electrophoretic mobility of the three-membered complex is dependent on bound second binding partner. Additionally, the three-membered complex is an indicator of the presence of analyte. Moreover, the electrophoretic mobility of said three-membered complex and the first binding partner are distinguishable. In certain embodiments, the electrophoretic mobility of the complex and the first binding partner are of opposite sign under certain conditions of pH.

A charge-modifying moiety attached to the second binding partner can further comprise a composite moiety. That is, the moiety which actually confers the charge to the second binding partner can be attached to the second binding partner via an intermediary. For example, in one embodiment of the present invention, nucleobases can be attached to the second binding partner via a polyamide such as an aminoethylglycine polymer. On the one hand, the nucleobases per se would actually confer the charge modification on the second binding partner even though attached via an intermediary. On the other hand, in this particular example, the second binding partner is effectively conjugated to a peptidyl nucleic acid (PNA). See, e.g., Nilsen et al., *Science* 254:497 (1991); Egholm et al., *Nature* 365:566 (1993), both references incorporated by reference herein. Thus, the charge-modifying moiety in this exemplary embodiment is, in fact, a composite moiety as contemplated herein. In essence, any analyte recognition site which is directly or indirectly conjugated with a charge conferring moiety falls within the definition of second binding partner as used herein and is suitable for use in the present invention. Equivalent composite moieties suitable to confer charge modifications on the second binding partner are within the knowledge of the ordinary skilled artisan and can be identified by routine experimentation.

In certain preferred embodiments, the composition comprises a complex wherein the second binding partner comprises a single-site charge modifier. That is, the second binding partner is derivatized at a single location such that it becomes charge-modified per se. For example, single-site charge modifiers suitable for use in the claimed invention include, but are not limited to, the following moieties: oligonucleotides, polyaspartic acid, polyglutamic acid, carboxymethylcellulose, polymaleic acid, polylactic acid, polysulfonic acid, and polyacrylic acid. Other single site charge modifiers include: polylysine, polyethyleneimines, polyarginine, and poly(diallyl dimethyl ammonium) salts. Currently, insofar as negative charge modifiers are concerned, polyT such as $polyT_{20}$ is currently preferred; polyA, polyC, or polyG can equally well be used. Other single site charge modifiers are polymers containing (—OH) groups such as polysaccharides or polydiols. Such groups will form complexes with borate if borate is included in the separation medium and impart a negative charge. Moreover, polyglutamic acid having 250 negative charges is currently preferred in certain other embodiments. For example, as described below in detail, polyglutamic acid conjugated to an F(ab') antibody fragment-is suitable for use as a second binding partner in the instant invention. Generally speaking, any charge-modifying moiety having approximately a range of 3 to 500 negative charges or 3 to 500 positive charges is suitable for use in the instant invention, however, the skilled artisan will be able to identify the charge best suited to his/her particular application using only routine experimentation.

In other currently preferred embodiments, the second binding partner comprises a multi-site distributed charge modifier. That is, a modification which alters the second binding partner's charge density is also suitable for use in the instant invention. For example, a modification which results in distribution of charge-modifying moieties attached at a plurality of sites on the second binding partner is suitable for use. Currently preferred are peptides such as $(Asp)_3$ (aspartic acid trimer) or $(Glu)_{10}$ (glutamic acid decamer) which are attached to a proteinaceous binding partner via derivatized lysine residues. Furthermore, it will be understood by the skilled practitioner that a second binding partner which is intrinsically sufficiently charge modified such that electroseparation of analyte-containing complex from unbound first binding partner can be achieved without a deliberate charge modification is also suitable for use as a second binding partner in the instant invention.

In accordance with the claimed invention, a composition comprising a three-membered complex of analyte, first binding partner, and second binding partner, as defined herein, exhibits an electrophoretic mobility different from that of unbound first binding partner. Moreover, the aforementioned electrophoretic mobility of the composition is dependent upon the second binding partner. Preferably, the electrophoretic mobility of the three-membered complex and the first binding partner are of opposite sign.

In certain embodiments, the claimed composition comprises a non-transient, i.e., non-intermediary, detectable three-membered complex which is amenable to electroseparation using techniques such as free zone and free flow capillary electrophoresis. As discussed above, detection of complex, not its individual component parts, is an indication of the presence of analyte. The invention further contemplates that, once complex formation occurs, no further manipulations of the complex is such as fractionation and/or dissociation into its component parts are required for analyte determination, either quantitative or qualitative. In a currently preferred embodiment, a complex comprising a nucleic acid analyte further comprises at least one non-nucleic acid binding partner. Similarly, a complex comprising two nucleic acid binding partners further preferably comprises a non-nucleic acid analyte. As discussed earlier, the compositions disclosed in WO 93 20236 contain nucleic acid analytes and polynucleotides transiently attached thereto. In fact, the compositions formed following the annealing and/or ligating steps of the methods disclosed therein can be characterized as two-membered or four-membered complexes. Furthermore, the disclosed compositions per se are not indicators of the presence, absence or concentration of the nucleic acid analyte.

Detectable or charge-modifying moieties can be attached to the above-described antibody fragments; derivatizing antibody fragments at the hinge region can be accomplished by known methods such as using detectable or charge-modifying moieties with thiol reactive groups such as maleimides or haloacetamides. The moieties accordingly introduced to the antibody fragment would be removed from the antibody recognition site and would not have any side effects on antibody-antigen recognition. This is an important consideration especially if large moieties such as enzymes or charge carriers are to be attached to an antibody. Thiol groups in an antibody can be generated through different routes such as: (i) pepsin digestion followed by reduction of the disulfides at the hinge region [F(ab')]; (ii) reduction of the entire antibody into two halves by cleavage of the disulfide bonds at the hinge region [$F(ab')_2$]; and (iii) chemical introduction via the use of various art-recognized bifunctional reagents.

Insofar as the first binding partner of the present invention is concerned, a currently preferred detectable moiety is the fluorescent moiety, rhodamine. Rhodamine can be successfully conjugated with F(ab') fragments, for example, using the above-described thiol chemistry and rhodamine iodoacetamide, Preparation of such first binding partner is within the skill of the ordinary artisan using well-known techniques and commercially available reagents. The use of an anti-rhodamife cartridge is suitable for the purification of rhodamine labeled F(ab') from excess $F(ab')_2$ and unlabeled F(ab').

Suitable second binding partners can be prepared using a single-site or multi-site charge-modifying approach. For single-site modification, it is suitable in some circumstances to use a charge carrier with a high number of charges such as polyglutamic acid (poly-Glu). Polyglutamic acid is available from Sigma [St. Louis, Mo.] at various degrees of polymerization (d.p.) and with a relatively narrow molecular weight distribution. For example, poly-Glu with a mean d.p. of 240 (molecular weight approximately 36,000; 241 negative charges) can be conjugated at the amine terminal with a commercially available bifunctional reagent. Activated poly-Glu can then be attached to an F(ab') antibody fragment to form the second binding partner of the instant invention. The use of thiol groups in the F(ab') hinge region which result from the reductive cleavage of F(ab')$_2$ for derivatizing poly-Glu has two advantages. First, there are only 2 or 3 such groups available for binding, and second, they are away from the antibody recognition side. Another single-site charge-modifying moiety suitable for use herein is the oligonucleotide polyT$_{20}$ (molecular weight approximately 6000; 20 negative charges).

Currently, commercially available polyamino acids with lower charge density are preferred, such as a copolymer of poly(Glu:Ala) (glutamic acid:alanine) with a molecular weight of approximately about 30,000, or a polyaspartic acid (poly-Asp) with a molecular weight of approximately about 8,900. Polyaspartic acid is preferred since it has a lower pKa, and its excess can be readily removed after conjugation with Fab' by gel filtration.

Protein-protein cross-linking can be obtained in various ways known in the art. For example, the N-succinimidyl group of the heterogeneous bifunctional cross linker, N-succinimidyl-6-maleimidocaproate, is first reacted with the terminal amino group of poly-Glu. This reaction is at neutral pH selective for amino groups. Unreacted crosslinker is then removed by conventional gel filtration using Sephadex G-25. In a second reaction, the thiol groups of the hinge of Fab' are selectively reacted at pH 6 with the maleimido group; at pH 6, the thiol group reacts 1000 times faster than amino groups. Because the cross linker has five CH$_2$ groups between its two binding sides, steric hindrance between Fab' and poly-Glu is minimal. See, e.g., Yoshitake et al., *J. Biochem.* 92:1413–1424 (1982), herein incorporated by reference.

As discussed above, the second binding partner can also comprise a multi-site charge-modifying moiety. This type of derivatization scheme distributes negative charges, for example, over the entire antibody molecule to lower the charge density. This can avoid the non-specific (ionic) interactions sometimes observed when a large charge-modifying moiety is attached at a single site on an antibody molecule. Antibody succinylation (or acylation) is a suitable method in this regard. By reacting the whole antibody molecule with succinic anhydride at room temperature, all epsilon amino-side chains (present in lysine residues) are converted to anhydride of carboxylic acid, resulting in a net loss of one positive charge and a net gain of one negative charge at neutral pH for each lysine residue. This results in an increase in the electrophoretic mobility of the antibody without any observed loss in binding activity. Furthermore, via covalent attachment to the antibody through the lysine amino-side chains, short polyamino acids, specifically poly-Glu (molecular weight approximately 1000) and a trimer of aspartic acid (molecular weight approximately 363) can introduce 11 and 4 negative charges, respectively, per lysine residue. Accordingly, the distribution of the charges over the entire antibody molecule, rather than at a single site, can be achieved.

The above-described multi-site conjugation scheme is based on a sequential amine-amine coupling using the heterobifunctional cross linker 2,3-dibromopropionyl-N-hydroxysuccinimide ester (SDBP) which is commercially available. In this case, the N-hydroxysuccinimide (NHS) end of the cross-linker is first reacted with the antibody molecule since this group is more labile at a lower temperature. Primary amines on the antibody molecule are modified with the cross linker molecules at 0–5° C., resulting in the release of NHS. The antibody now contains alkyldibromide groups on its surface which are thereafter coupled to the primary amine terminal of the polyamino acid at room temperature.

Another heterobifunctional reagent which is contemplated for protein modification in the instant invention is sulfosuccinimidyl [4-iodoacetyl]amino benzoate (sulfo-S1AB). A primary amino group of (Asp)$_3$ or (Glu)$_7$ is first reacted with sulfo-S1AB via the N-hydroxysuccinimide ester. This results in the formation of an amide bond between sulfo-S1AB and the peptide via the release of the N-hydroxysuccinimide. Separately, sulfhydryl groups are introduced into the second binding partner using Traut's reagent that reacts with the epsilon amino side chains at pH >7.0. Thereafter, the sulfhydryl groups react with the iodoacetyl group of the sulfo-S1AB modified (Asp)$_3$ or (Glu)$_7$ resulting in a stable thio ether linkage.

Generally, to obtain good sensitivity, it is important to remove unconjugated F(ab'), F(ab')$_2$, and undigested antibodies from any of the above-described preparations. Unconjugated antibody fragments and/or antibodies can reduce assay sensitivity by competing with the derivatized reagents when binding the antigen. Towards this end, the course of pepsin digestion can be monitored electrophoretically over time to determine optimal conditions. For example, aliquots of the pepsin digestion mixture can be taken over an eight hour period followed by both native and denaturing gel electrophoresis. In optimal circumstances, digestion of the antibodies is complete after one hour and the F(ab')$_2$ produced is resistant to further cleavage by pepsin.

Short SPE (solid-phase extraction) columns with activated sulfonic and carboxy groups would be suitable for the removal of unconjugated F(ab') with poly-Glu conjugates. By using a pH of about 5.0, unconjugated F(ab') adsorbs onto the columns while the highly charged F(ab')-poly-Glu conjugate elutes with the void volume. Conventional chromatographic fractionation using Sephadex G-150 is also useful.

In another aspect, the claimed invention provides methods for detecting the presence, absence or concentration of an analyte using ultrafast electroseparation analysis. When practiced in accordance with the invention, the methods utilize the above-described compositions as indicators of the presence, absence or concentration of analyte in a sample. In one embodiment, first binding partner and second binding partner are combined with a sample to produce a mixture in which, if analyte is present, a three-membered complex forms. As used herein, the term "combine" is intended to mean any process by which multiple components are brought together for subsequent interaction at the molecular level. Combining can occur simultaneously or sequentially. It is contemplated that the above-described three-membered complex can be detected by either simultaneously or sequentially adding the first and second binding partners to a sample. Typically, the method is conducted using an unfractionated mixture obtained as described above, however, detection of certain analytes using the method of the instant invention may necessitate use of a fractionated mixture.

Combining sample and binding partners yields a "mixture." In some instances the mixture will comprise a three-membered complex, e.g., when analyte is present in the sample, while in other instances the mixture will comprise uncomplexed binding partners, e.g., when first and second binding partners do not bind to analyte. In certain embodiments of the instant method, combining can be followed by incubating such that components in the mixture are afforded a more prolonged opportunity to interact and form complex. It may be necessary to incubate the mixture of certain analytes and/or binding partners for a time sufficient to permit complex formation to proceed to equilibrium. The skilled artisan will be able to determine when it is appropriate and/or necessary to include the incubating step using routine experimentation.

As disclosed herein, it is contemplated that a three-membered complex comprising analyte, first binding partner and second binding partner can form under a variety of different circumstances. For example, complex formation can occur when all components are in solution, e.g., in a sample of body fluid or physiological buffer. Complex formation can occur when one or more components are disposed within an electroseparation channel, either dispersed in pre-formed zones or reversibly immobilized in pre-chosen regions of the channel. In such alternative embodiments, a prerequisite for complex formation is that analyte and binding partners have sufficient opportunity to interact prior to actual electroseparation analysis. As discussed above, the complex utilized in accordance with the method of the instant invention preferably exhibits an electrophoretic mobility different from that of unbound first binding partner upon electroseparation analysis, thereby permitting ready and reliable detection of the analyte-containing complex.

According to at least one embodiment disclosed herein, a mixture of sample and binding partners can be disposed within an electroseparation channel. A channel preferably is a capillary of approximately about 500$\mu$ in diameter. An electrical potential is then applied to the electrically conductive medium contained within the channel to effectuate migration of the components within the mixture. A currently preferred electrically conductive medium is a biological buffer which may additionally contain zwitterions. A particularly preferred conductive medium is amino caproic acid-acetic acid containing 0.1% methylcellulose. A currently preferred zwitterionic compound is AccuPure™ (Waters Corp., Milford, Mass.), a quarternary amine-sulfonic acid compound functional over a broad pH range. In general, zwitterionic compounds are useful with uncoated capillary electroseparation channels by preventing and/or minimizing adsorption of proteins to the capillary walls. Identification of equivalents suitable for use in the methods and apparatus of the present invention is well within the skill of the ordinary practitioner and would require no more than routine experimentation.

Following the step of electroseparation, the claimed method provides for detection of the complex. Detection can be achieved by methodologies including, but not limited to: absorbance of ultraviolet radiation, absorbance of visible radiation, fluorescence, refractive index, Raman, mass spectrometry, electrochemistry, and conductivity. Detection by fluorescence is preferred.

The methods of the instant invention can be used to detect two or more different analytes in a sample. The skilled practitioner is able to choose among possible binding partners, detectable moieties, and charge-modifying moieties such that the presence, absence or concentration of two or more different analytes can be determined using the methods disclosed herein and routine experimentation.

The experimental parameters of the claimed methods which may be varied include, but are not limited to, electro-osmostic flow, electrophoretic mobility, chemistry of the electrophoretic medium, pH, temperature, ionic strength, viscosity, sample volume, electric potential, length of capillary, detection method, and the concentrations of the reacting species. These parameters may be optimized for any electroseparation analysis performed. Varying one or more of these parameters allows one of skill in the art using routine experimentation to exploit the invention, and confers versatility on the claimed methods.

Control of electro-osmotic flow allows for reproducible analysis. Electro-osmotic flow is an inherent factor in the electrophoretic velocity of each chemical species present in the system, and can affect the duration of contact of the reagents, as well as migration of the detectable complex. Consistent and reproducible electro-osmotic flow is essential for quantitative analyses according to the invention, since the electrophoretic migration rate of the complex differentiates it from unbound first binding partner. Electro-osmotic flow can be increased, decreased or reversed by altering the nature of the coating of the capillary. Coatings can alter the charge on the capillary wall and thereby alter the zeta potential at the capillary solution interface. Also, the capillary coating can affect the local viscosity at the wall and hence directly affects electro-osmotic flow by increasing or decreasing the solution drag on molecules in the system. In addition, the pH of the electrophoretic medium as well as its ionic strength alter the zeta potential at the capillary/solution interface, thereby changing the solution flow.

The electrophoretic velocity of a chemical component is determined by its electrophoretic mobility in an electric field and the electro-osmotic flow. The electrophoretic mobility of the component can be affected by the nature of the electrophoretic medium, e.g., pH, ionic strength, and viscosity. An electrophoretic medium, e.g., free solution, can be chosen for physical properties which will selectively impede the electrophoretic mobilities of certain components of the system. For example, adding a sieving agent to the medium can increase the molecular drag of the species and, therefore, decrease electrophoretic mobility. In addition, the degree of ionization of charged molecules in the system can be selectively altered by buffering the medium at various pHs and varying the ionic strengths. Differences in electrophoretic mobility can be amplified by the selection of electrophoretic medium, pH, ionic strength, and viscosity. Such parameters can be optimized by one of ordinary skill in the art using only routine experimentation.

The volume of sample and binding partners, as well as the order in which they are introduced into the system, will be chosen in light of other experimental parameters, e.g., the relative electrophoretic mobilities of analyte and binding partners, the concentration of analyte or partner within a zone, and kinetics of the complex formation itself. Generally, it is desirable that the zone containing a component having a higher electrophoretic velocity will be introduced into the capillary later than the slower moving component zone, so that the faster component may overtake the slower component, provided the electrophoretic velocities of the components are oriented in the same direction.

The electric potential required to impart electrophoretic motion is typically applied across the capillary by a high voltage source operated at electric field strengths generally ranging from several hundred volts per centimeter to several thousand volts per centimeter. See U.S. Pat. Nos. 4,865,706 and 4,865,707 hereby incorporated by reference. The application of the potential can be controlled either via manual operation, a waveform generator, or computer control.

The rates of migration of chemical species in capillary electrophoresis are directly proportional to the electric field applied due to electrophoretic and electro-osmotic effects. The strength of the electric.field does not affect the relative rates of migration of chemical species, however, the assay time, the time at which zonal engagement occurs in some embodiments, and the total time of interpenetration and, therefore, complex formation can be dictated by the applied potential in certain embodiments of the instant invention. For example, in certain embodiments of the instant invention, once the analyte and partner zones become engaged, the applied potential determines the nature of the contact: dynamic at potentials greater than zero and static at zero potential. As used herein, low potential refers to approximately 1 to 100 volts/cm; high potential refers to approximately 100 to 300 volts/cm. Lower electric field strengths result in slower movement of chemical species, thereby increasing the contact time of two zones.

Higher potentials offer the advantage of speed as the magnitudes, but not relative values, of the rates of migration of the species involved in the assay increase proportionally. In some embodiments, high potentials also offer the ability to mix zones rapidly and, for those reactions for which sufficient reaction time and sensitivity are not a concern, to minimize analysis time. Given knowledge of the demands of a given chemical system involved in an assay, one of skill in the art may easily choose the potential so as to optimize each of the stages involved in the assay by routine experimentation. For example, the zonal merging stage may be done at high potential to induce rapid, uniform mixing; the ensuing complex formation phase may be done at lower potential to allow sufficient time for the complex to form and to provide maximum sensitivity. The potential may then be increased to sweep the detectable complex past the detector and minimize analysis time.

As discussed further below, the length of capillary used in combination with the applied potential determines the strength of the electric field and thus, also affects the rates of migration of each chemical species. In addition to the overall length of the capillary, the separation length, i.e., the length between the point of introduction into the capillary and the position at which the complex passes the detector, is another parameter which affects the assay. The separation length affects the time available to perform the mixing and complexing phases of certain embodiments of the methods disclosed herein. For uninterrupted potential, a longer separation length is often necessary.

Kinetic parameters may also be altered by the selection of factors such as pH, ionic strength, viscosity, and temperature. For example, complex formation can-be highly dependent on temperature. In some embodiments, use of a thermostated capillary electrophoresis system allows for the selection of a reaction temperature. Furthermore, the pH and ionic strength of the electrophoretic medium may be varied.

The electrophoretic medium is critical as it is responsible for exploiting physical characteristics of the reagent species in order to impart the variability in electrophoretic velocity necessary to perform the physical separations sought.

In another aspect, the claimed invention provides an apparatus for detecting the presence, absence or concentration of an analyte in a sample by electroseparation analysis. When utilized in accordance with the methods and compositions of the instant invention, the apparatus permits qualitative and quantitative detection of an analyte in a sample. As disclosed herein, the apparatus typically comprises an electroseparation channel containing electrically-conductive medium; an injection zone; a mixture comprising sample; first binding partner and second binding partner; and a source of voltage. Other embodiments comprise an additional means for disposing sample, binding partners, and/or three-membered complexes within the channel.

Activation of the electrical potential in one embodiment of the apparatus results in the three-membered complex and unbound first binding partner resolving into two opposite moving zones, one zone containing the complex and the other containing unbound first binding partner. In certain other embodiments, in which the electrophoretic mobility of three-membered complex is opposite the electro-osmotic flow of the apparatus, the complex is injected into the channel electrokinetically. In all embodiments contemplated herein, the three-membered complex migrates electrophoretically at a rate distinguishable from that of unbound first binding partner for the reasons set forth above.

In the claimed apparatus, electroseparation is preferably achieved by electrophoresis. Free zone electrophoresis is currently preferred. Specifically, free zone electrophoresis is an electroseparation method conducted in a non-sieving medium containing electrolytes in which an electric field is applied parallel to the flow of medium. Typically, free zone electrophoresis is conducted as a batch process within a capillary permitting high resolution and enhanced sensitivity. Capillary electrophoresis, however, is fundamentally limited as a preparative system because of the small dimensions of the capillary. Increasing capillary diameter is not an acceptable solution since resolution and sensitivity are compromised. In contrast, free flow electrophoresis is suitable for preparative applications. Accordingly, another currently preferred embodiment is free flow electrophoresis. Specifically, free flow electrophoresis is an electroseparation method also conducted in a non-sieving medium with the same composition of electrolytes in which an electric field is applied perpendicularly to a hydraulically-pumped flow of the carrier background electrolytes. Charged species within the electroseparation channel are deflected at different angles from the straight direction of flow by the electric field according to their respective electrophoretic mobilities. Typically, continuous free flow electroseparation is conducted in a flowthrough chamber, thereby permitting the preparative capacity of the system to be enlarged.

In a preferred embodiment of the invention, free zone electrophoresis is conducted within an electroseparation channel configured as a capillary. As used herein, the term "capillary" is intended to include a channel of less than approximately 500$\mu$ in diameter fabricated of fused silica, for example. In certain embodiments, untreated silica is preferred. For example, it would be understood by the skilled artisan that untreated silica is preferred when operating at high pH, e.g., pH >9.5. In certain other embodiments, treated silica is preferred. For example, the skilled artisan would use treated silica when operating in the physiological pH range or if it is desired to eliminate electro-osmotic flow. Insofar as the present invention is concerned, a treated capillary includes, but is not limited to, one comprising an inner wall with a covalent modification resulting from reaction with epoxy polymers, polyethyleneimine, aminopropyl-sialyted coatings, and polyacrylamide. Additionally, a capillary inner wall can be dynamically modified, e.g., by exposure to a amino derivatives, cationic polymers, and cationic fluorosurfactants. Further considerations for embodiments comprising capillaries in accordance with the present invention are described in detail below.

Typically, the claimed apparatus includes a capillary with an inlet end and an outlet end. The capillary may be a pulled glass or fused silica tube or any equivalent means for electrophoresing micro-samples. The capillary can have a diameter less than about 500$\mu$ and most preferably about 25 to 100$\mu$. The length of the capillary can be in the range of about 0.5 to 5,000 centimeters from the inlet end to the outlet end, preferably about 2 to 100 cm. Capillaries which operate under electric fields of from several hundred volts per centimeter up to several thousand volts per centimeter or more are preferred. See U.S. Pat. Nos. 4,865,706 and 4,865,707, hereby incorporated by reference. Moreover, the capillaries employed in the instant invention are typically constructed of silica which is coated on the outer surface with an agent, such as polyimide, to prevent breakage due to the fragile nature of silica.

In the methods of the invention, it is frequently advantageous to use capillary coatings. These coatings offer several advantages to the use of uncoated silica. The ionization of silanol groups produces a negatively-charged silica surface. Positively-charged analytes, such as proteins, adsorb to the negatively-charged wall thereby altering the zeta potential at the silica/solution interface. Disruption of the zeta potential alters the electro-osmotic flow and may decrease reproducibility and reduce recovery of product. Variability in electro-osmotic flow is particularly detrimental in quantitative analyses. Capillary surface modification may also be useful for controlling electro-osmotic flow. The ability to regulate the electro-osmotic flow serves as a powerful tool for practicing certain embodiments of the invention. For example, the process of electrophoretic mixing of zones as well as the migration of the detectable product is dependent upon the electrophoretic velocities and, therefore, the electro-osmotic flow of the system.

Those coatings which have been employed in capillary electrophoresis include the covalent modification of the silica surface as well as the use of buffer additives to dynamically modify the capillary wall. Representative examples of the covalent modification technologies include epoxy polymers (Towns et al., 1992, *Journal of Chromatography* 599:227), polyethylene-imine (Towns and Regnier, 1990, *Journal of Chromatography* 516:69), aminopropyl-sialylated coatings (Mosely et al., 1991, *Anal. Chem.* 63:109), polyacrylamide (Cobb et al., 1990) *Anal. Chem.* 62:2478; Hjerten, 1985, *Journal of Chromatography* 471:429). Representative examples of the use of dynamic coatings include amine additives (Lauer and McManigill, 1986, *Anal. Chem.* 58:166; Nielsen et al., 1989, *Anal. Biochem.* 177:20), cationic polymers (Wiktorowicz and Colburn, 1990, *Electrophoresis* 11:769), and cationic fluorosurfactant (Emmer et al., 1991, *Journal of Chromatography* 547:544). Covalent modification coupled to adsorbed dynamic coatings has also been utilized, such as in the use of nonionic surfactants adsorbed to silane-derivatized surfaces (Towns and Regnier, 1991, *Anal. Chem.* 63:1126). In the case of polyacrylamide coatings, it is currently preferred that such coatings are deposited following siloxane crosslinking treatments such as those disclosed in U.S. Pat. No. 5,322,608 by Karger et al.

In yet another embodiment, the claimed apparatus comprises a solid substrate microfabricated to define an electroseparation channel, such as by engraving, chemical, or ablation etching with lasers. The electroseparation channel is microfabricated as a flow-through passage of suitable depth, width and length. Currently, a preferred embodiment comprises channel depth and width between about 0.1 $\mu$m and 1000 $\mu$m, preferably between about 10 $\mu$m and 1000 $\mu$m and more preferably between about 5 $\mu$m and 100 $\mu$m. Suitable parameters for defining width, depth and length can be readily determined by the skilled artisan using only routine experimentation. Additionally, in accordance with the present invention, the apparatus can comprise a plurality of channels. As disclosed in more detail below, preferred embodiments of the apparatus can be microfabricated using silicon, silica, or glass. A free flow electrophoresis device integrated onto a silicon chip for continuous sample pretreatment is described by Raymond et al., *Analytical Chemistry* 68:2858–2865 (1994). In another preferred embodiment, the apparatus is microfabricated using an organic polymer. Organic polymers suitable for use in the apparatus are moldable, may be translucent or, preferably, transparent, to the extent necessary to permit detection by a particular detecting means. Exemplary organic polymers include, but are not limited to, polycarbonate and polystyrene. It will be understood that identification of equivalents is within the knowledge of one of ordinary skill in the art.

The claimed invention provides a family of small, mass produceable, optionally disposable, apparatus for detecting a particular analyte in a fluid sample. The apparatus may comprise a solid substrate, typically on the order of a few millimeters thick and approximately 0.2 to 2.0 centimeters square, that is microfabricated to define a flow-through channel and optional sample inlet port. The apparatus includes at least one flow-through channel. The flow-through channel can also provide at least one region which contains a binding moiety disposed therein. Optionally, the binding moiety may be immobilized within the channel. As disclosed herein, the apparatus can be used in a wide range of rapid diagnostic tests. Alternatively, the apparatus can be fabricated with two or more channels which comprise two or more different binding moieties for different analytes, allowing two or more assays to be conducted simultaneously. The apparatus may optionally be disposable at the conclusion of the assay.

The apparatus of the invention for ultrafast electroseparation analysis can be designed and fabricated in large quantities from a solid substrate material. Silicon, silica, and glass are preferred because of the enormous body of technology permitting their precise and efficient fabrication, but other materials may be used including polymers such as polytetrafluoroethylenes. For example, the apparatus of the present invention can be fabricated inexpensively in large quantities from a silica substrate by any of a variety of micromachining methods known to those skilled in the art. The micromachining methods available include film deposition processes such as spin coating and chemical vapor deposition, laser fabrication or photolithographic techniques such as UV or X-ray processes, or etching methods including wet chemical processes or plasma processes. (See, e.g., Manz et al., *Trends in Analytical Chemistry* 10:144–49 (1991).) Flow channels of varying widths and depths can be readily fabricated, i.e., with cross-sectional dimensions on the order of 0.1 to 1,000 $\mu$m.

Additionally, the substrate containing a microfabricated flow-through channel may be covered and sealed with a thin anodically bonded glass cover. Other clear or opaque substrates can be sandwiched. Alternatively, a silicon substrate may be sandwiched between two glass covers. The use of a transparent cover results in a window which facilitates dynamic viewing of the channel contents and allows optical probing for detection either visually or by machine. Other fabrication approaches may be used.

In one currently preferred embodiment, illustrated schematically in FIG. 1, apparatus 10 may include a fused silica substrate 12, microfabricated with a flow-through channel 20, which optionally can be provided with binding moieties capable of binding a preselected analyte. Buffer solution and reagent fluid may be provided to the flow-through channel 20 via ports 16 which are fabricated on either end of the flow-through channel 20. Sample and reagents may be added via port 24. Port 26 may be used to receive excess sample solution ensuring that a representative sample is present in the flow-through channel 20. The microfabricated silica substrate 12 can be covered with a second fused silica substrate 30. During an analysis, the device 10 may be placed in a support structure with fluidic and electrical connections to the ports 16, 24, and 26. The dimensions of channels may vary in the range from approximately 10 μm to 1,000 μm wide and approximately 5 μm to 100 μm in depth. The scale of the apparatus depicted in FIG. 1 is exaggerated for clarity.

The capacity of the apparatus disclosed herein is very small and therefore reduces the amount of sample fluid required for an analysis. For example, in a 1 cm×1 cm silicon substrate, having on its surface an array of 500 grooves which are 10 microns wide×10 microns deep×1 cm ($10^4$ microns) long, the volume of each groove is $10^{-3}$ μL and the total volume of the 500 grooves is 0.5 μL. The low volume of the apparatus of the instant invention enhances the reaction rates of binding assays conducted in the channel of certain embodiments contemplated herein. For example, in a channel containing a surface coating of an immobilized binding moiety, as predicted by the Law of Mass Action, as the volume of the channel decreases, the surface area to volume ratio of the binding moiety in that region increases, which results in an increased rate of intermolecular reaction between an analyte and the reversibly mobilized binding moiety. The entire channel system of the claimed apparatus may preferably have volumes on the order of less than 10 μL. In certain embodiment, enzyme amplification is used, in which instance detection regions are small enough in at least one dimension to favor fast kinetics. The flow-through channels of the instant apparatus can be microfabricated with microliter volumes, or alternatively nanoliter volumes or less, which advantageously limits the amount of sample and/or reagent fluids required for an assay.

The above-described apparatus containing a flow-through channel can be further combined with an appliance for delivering and receiving fluids to and from the apparatus. The appliance may include means, such as a pump, for forcing the sample through the flow system. After a biological fluid suspected to contain a particular analyte is applied to the inlet port, the pump is actuated to force the sample into the apparatus and the flow-through channel. Alternatively, a sample may be injected into the apparatus by the appliance, or the sample may enter the flow-through channel through the inlet port by capillary action. Other embodiments of appliances may be fabricated for use with differently configured apparatus.

As discussed previously, binding moieties can be introduced into the channel or may be reversibly immobilized in the channel after its manufacture by, for example, physical absorption or chemical attachment to the surface of the flow-through channel or to a solid phase reactant such as a polymeric bead disposed in the detection region.

As in the case of an apparatus comprising a capillary, the surfaces of the electroseparation channels in silicon substrates also can be chemically activated and reacted with a protein, lipid, polysaccharide or other macromolecule to form a coated surface within the channels. Techniques for the chemical activation of siliceous surfaces are available in the art. (See, e.g., Haller in: *Solid Phase Biochemistry*, W. H. Scouten, Ed., John Wiley, New York, pp. 535–597 (1983); and Mandenius et al., *Anal. Biochem.*, 137:106–114 (1984) and 170:68–72 (1988) and Mandenius et al., *Methods in Enzymology*, 137:388–394). There are a number of techniques in the art for attaching biomolecules to silicon. For example, enzymes may be immobilized on silicon devices via entrapment in a photo-crosslinkable polyvinyl alcohol (Howe et al., *IEEE Transactions Electron Devices*, ED33:499–506 (1986) or attached indirectly using pre-formed membranes (Hanazato et al., *IEEE Transactions Electron Devices*, ED33:47–51 (1986). A hydrophobic bilayer glycerol monooleate coating may be fabricated on a silicon substrate. Fromherz et al., *Biochim. Biophys. Acta*, 1062:103–107 (1991).

Protein conjugation and immobilization techniques known in the art can also be adapted for use with activated siliceous surfaces. Kennedy et al., *Clin. Chem. Acta*, 70:1–31 (1976); Sankolli et al., *J. Imm. Methods*, 104:191–194 (1987); Kricka et al., *Clin. Chem.*, 26:741–744 (1980); and DeLuca et al., *Arch. Biochem, Biophys.*, 225:285–291 (1983). Known chemistries in the art may be adapted for use in attaching biomolecules to coated or uncoated silicon channel surfaces. A binding moiety such as an antigen binding protein, a polynucleotide probe, or one of a ligand/receptor pair may be attached to the silicon channel surfaces. The surface coated apparatus can be utilized in any of a wide range of available binding assays known in the art such as immunoassays, enzymatic assays, ligand/binding assays, polynucleotide hybridization assays, and cell surface binding assays. The detection of a particular analyte can be implemented by selecting the appropriate binding moiety coated on the surface of the channel.

A large number of binding assay protocols known in the art can be exploited in the electroseparation channel apparatus of the invention, for example, immunochemical assay techniques such as enzyme-linked immunoassays. (See Bolton et al., *Handbook of Experimental Immunology*, Weir, D. M., Ed., Blackwell Scientific Publications, Oxford, 1986, vol. 1, Chapter 26, for a general discussion on immunoassays.)

Any conventional method of detection may-be used in the apparatus of the present invention, including those used in more conventional capillary electrophoresis methods. A detection method is chosen which allows for detection of any suitably detectable physical property of a species. These detection systems include, but are not limited to, absorbance of ultraviolet or visible radiation, fluorescence, refractive index, Raman, mass spectrometry, electrochemical, and conductivity. Detection of the electrophoretically distinct complex of the instant invention may occur at a discrete position along the length of the capillary, off-line, or by imaging the entire length of the capillary (Wu et al., 1992, *Anal. Chem.* 54:219), hereby incorporated by reference.

In yet another aspect, the claimed invention provides kits for detecting the presence, absence or concentration of an analyte using electroseparation analysis. Preferred embodiments of kits are configured to detect clinically relevant analytes in biological samples. In one embodiment, the kits of the present invention comprise reagents and an apparatus.

The above-mentioned kit reagents comprise a detectable moiety for attachment to a first binding moiety, and a charge-modifying moiety for attachment to a second binding moiety. In one embodiment, the first and second binding moieties are available separately from the detection and charge moieties. Typically, the first binding moiety is competent to bind to a first binding site on an analyte to be detected, and the second binding moiety is competent to bind to a second binding site on the analyte to be detected. In this instance, the kit further comprises attachment reagents with which said detectable moiety and charge-modifying moiety can be attached to the first and second binding moieties, respectively. Upon attachment, the first and second binding moieties become the first and second binding partners, respectively, described above. Accordingly, a first binding partner and a second binding partner created using the kit reagents of the instant invention are competent to bind to analyte, if present in a sample, thereby forming a three-membered complex which exhibits an electrophoretic mobility different from that of unbound first binding partner during electroseparation analysis.

In certain other embodiments of the claimed kits, the reagents comprise a first binding partner having a detectable moiety attached thereto, and a second binding partner having a charge-modifying moiety attached thereto. Again, if present in a sample, the kit reagents comprising first and second binding partners will form a complex with analyte which, upon electroseparation analysis, will migrate differently than unbound first binding partner. Thus the kit reagents of the present invention provide a means for detecting analyte in a sample.

In certain embodiments, the kits of the present invention further provide an electroseparation apparatus comprising a channel or a plurality of channels. It is contemplated that diagnostic kits practiced in accordance with the instant invention optionally provide a multiplicity of disposable apparatus. In yet other embodiments of the invention, the kit provides an electroseparation apparatus comprising a capillary or plurality of capillaries as defined herein.

It will be apparent to those skilled in the art that various modifications and variations can be made in the compositions, methods, apparatus, and kits of the present invention without departing from the spirit or scope of the invention. Thus, it is intended that the present invention cover the modifications and variations of this invention, provided they come within the scope of the appended claims and their equivalents. Practice of the invention will be more fully understood from the following examples, which are presented herein for illustration only and should not be construed as limiting the invention in any way.

EXAMPLE 1

Preparation and Characterization of Binding Partners (a) In some embodiments, binding partners comprising a half-antibody produced using 2-mercaptoethylamine as a reducing agent were found suitable for use in the instant invention. Moreover, attaching the detectable moiety rhodamine to such an antibody using rhodamine iodoacetamide was successful at a dye-to-protein ratio of 0.96. The antibody fragment to which rhodamine was attached retained the binding affinity for its corresponding analyte.

(b) In other embodiments, binding partners comprising F(ab')$_2$ or F(ab') fragments produced using a matched pair of antibodies were found suitable for use in the instant invention. In one embodiment, the method included providing as the conjugated binding partner an Fab' fragment of an antibody labeled at a reactive sulfhydryl group with a detectable moiety; combining the detectable Fab' fragment with a sample that may contain the analyte; separating the detectable complex formed from any unreacted labeled detectable binding partner using capillary electrophoresis; and, detecting the complex. In a currently preferred embodiment, the Fab' fragment was conjugated at a single sulfhydryl group, the detectable moiety attached to the Fab' fragment was a fluorescent dye, and the elements of the mixture were concentrated in an electric field using a technique such as isoelectric focusing or isotachophoresis.

In other currently preferred embodiments of the present invention, an Fab' fragment of an antibody having a reactive sulfhydryl group (for subsequent attachment of a detectable moiety) was produced by cleaving the antibody with the proteolytic enzyme pepsin to obtain one F(ab')$_2$ fragment, composed of two disulfide-connected Fab units plus the hinge region, and small peptides of the Fc portion. The disulfide-bonded F(ab')$_2$ was then reduced to obtain two Fab' fragments. Preferably, intrastrand disulfide bonds are formed by oxidation, producing individual Fab' fragments each having a single reactive sulfhydryl group.

A conjugated Fab' fragment was typically prepared by: providing an Fab' fragment possessing a reactive sulfhydryl group; providing a detectable moiety having a site reactive with the reactive sulfhydryl group of the Fab' fragment; and mixing together the Fab' fragment and the detectable moiety so that the reactive sulfhydryl of the Fab' fragment reacts with the reactive site of the detectable moiety to form a detectable Fab' fragment.

As is well-known in the art, antibodies possess different activities associated with different sites on the antibody molecule. For example, analyte binding activity is associated with the variable region of the heavy chain ($V_H$) and the variable region of the light chain ($V_L$) domains located on the Fab fragment, whereas effector functions such as complement fixation and cell membrane receptor interaction are usually associated with the Fc fragment. It will be understood by the skilled artisan that using an antibody fragment in a binding assay makes it possible to exploit the activity of one portion of the molecule without interference from other domains.

For use in the instant invention, an antibody can be selectively cleaved into fragments, each having discrete activities, using a variety of art-recognized cleavage techniques. For example, papain cleaves the antibody into two Fab fragments and one Fc fragment containing the interchain disulfide bonds. By contrast, cleavage with pepsin produces one F(ab')$_2$ fragment and small peptides of the Fc portion. The resulting F(ab')$_2$ fragment is composed of two disulfide-connected Fab units, plus the hinge region. The disulfide-bonded F(ab')$_2$ fragment can be reduced to obtain two Fab' fragments, each with one or more free thiol groups. These reactive thiol groups of such a pepsin-generated Fab' unit provide useful sites (one or more) to attach extrinsic moieties such as fluorophores, chromophores, or binding ligands.

In one currently preferred embodiment, mouse monoclonal IgG, antibodies (Pierce; Rockford, Ill.) were cleaved with pepsin, and the resulting F(ab')$_2$ fragments were isolated and treated with a reducing agent such as dithiothreitol, dithioerythritol, or β-mercaptoethylamine to reduce the three connecting disulfide linkages and produce Fab' fragments. An intrachain disulfide bond between cysteine residues was formed by oxidation in order to provide only a single reactive thiol group per Fab' molecule. The free sulfhydryl group on each Fab' fragment was then conjugated with tetramethylrhodamine iodoacetamide (Molecular Probes; Eugene, Ores.) or cyanine, a fluorescent dye composed of two quaternized heteroaromatic bases joined by a polymethine chain (See, e.g., Ernst. et al., *Cytometry* 10:3–10 (1989), hereby incorporated by reference herein). The fragments were purified before use, e.g., by Imobiline gel electrophoresis (isoelectric focusing) (Pharmacia).

(c) With respect to charge-modifying moieties and conjugates thereof, commercially-obtained polymers of poly-Glu were first characterized by determining their electrophoretic mobility under several conditions. For example, using an untreated electrophoresis column, poly-Glu (molecular weight approximately 36,000; 241 negative charges) was observed to migrate against the electroosmotic flow at pH 5.2 in 30 seconds. At a higher pH (>6.5), the use of buffer additives such as methyl cellulose (0.1%) has been determined to be necessary to bring about the elution of poly-Glu against the electro-osmotic flow. Also, preparations of poly-Glu were fractionated using Sephadex G-50 with a size exclusion of approximately 30K to reduce the molecular weight distribution and remove small poly-Glu molecules.

Currently preferred are charge carriers with a high number of charges. For example, polyglutamic acid is available from Sigma [St. Louis, Mo.] at various degrees of polymerization (d.p.) and with a relatively narrow molecular weight distribution.

In some embodiments, poly-Glu with a mean d.p. of 240 was conjugated at the amine terminal with a bifunctional reagent. The activated poly-Glu was then conjugated with an F(ab') fragment to form the second binding partner of the instant invention.

In currently preferred embodiments, poly-Glu with its terminal amino group was conjugated with the thiol group in the hinge region of a Fab' available for such chemistries after the reductive cleavage of the $F(ab')_2$. The use of thiol groups in the hinge region for the conjugation of poly-Glu has two advantages. First, there are only 2 or 3 such groups available for binding, and second, they are away from the antibody recognition side.

Certain of the embodiments of the instant invention were practiced using protein-protein crosslinking chemistries, and modifications thereof, previously described by Yoshitake et al., *J. Biochem.* 92, 1413–1424 (1982). For example, the N-succinimidyl group of the heterogeneous bifunctional cross linker N-succinimidyl-6-maleimidocaproate (present in a 100×excess) was first reacted with the terminal amino group of the poly-Glu. This reaction proceeded at neutral pH which is selective for amino groups. Unreacted crosslinker was subsequently removed by Sephadex G-25. In a second reaction, the thiol groups of the hinge of Fab' were selectively reacted at pH 6 with the maleimido group. At this pH the thiol groups reacted 1000 times faster than amino groups. The cross linker has five $CH_2$ groups between its two binding sides which minimized any sterical hindrance between Fab' and poly-Glu. Equivalent chemistries suitable for use herein will be obvious to the skilled practitioner.

Selected oligonucleotides, such as $polyT_{20}$ (molecular weight approximately 6000; 20 negative charges), as well as other poly-Glu polymers (molecular weight approximately 36,000; 241 negative charges) have also been found to be suitable moieties for modifying the charge of the second binding partner as disclosed herein.

Other suitable moieties for single-site charge modification include a random equimolar copolymer of glutamic acid, alanine, and tyrosine (molecular weight approximately 40,000; lower charge density). Still other polyamino acids with lower charge density that are commercially available include a copolymer of poly(Glu:Ala) (glutamic acid:alanine) with a molecular weight of approximately 30,000 and a poly(aspartic acid) with a molecular weight of approximately 8,900. Poly(aspartic acid) is preferred since it has a lower pKa, and its excess was readily removable after conjugation with Fab' by gel filtration. Identification of equivalents is within the skill of the ordinary artisan.

All of the above-described conjugation schemes relate to single-site modifications. As discussed earlier, however, the present invention also contemplates multi-site modifications. An exemplary multi-site modification scheme follows.

(d) This particular conjugation scheme distributed negative charges over the second binding partner, e.g., antibody molecule, to lower the charge density. This avoided non-specific (ionic) interactions sometimes observed when a large charge moiety is attached at a single site. For example, by reacting intact antibody with succinic anhydride at room temperature, all epsilon amino-side chains (present in lysine residues) were converted to anhydride of carboxylic acid, resulting in a net loss of one positive charge and a net gain of one negative charge at neutral pH for each lysine residue. This resulted in an increase in the electrophoretic mobility of antibody by roughly a factor of 2 without any observed loss in binding activity. In a currently preferred embodiment, antibody was covalently attached through lysine amino-side chains to short polyamino acids, specifically poly-Glu (molecular weight approximately 1,000) and a trimer of aspartic acid (molecular weight approximately 363) which introduced 8 and 4 negative charges, respectively, per lysine residue. This ensured the distribution of charges over the entire antibody rather than at one site.

The above-described multi-site conjugation scheme is based on a sequential amine-amine coupling using the heterobifunctional cross linker 2,3-dibromopropionyl-N-hydroxysuccinimide ester. Specifically, the N-hydroxysuccinimide end of the cross-linker was first reacted with the antibody since this group is more labile at a lower temperature. Primary amines on the antibody were modified with the cross linker molecules at 0–5° C., resulting in the release of NHS. The antibody then contained alkyldibromide groups on its surface which were thereafter coupled to the primary amine terminal of the polyamino acid at room temperature.

EXAMPLE 2

Figure 2:
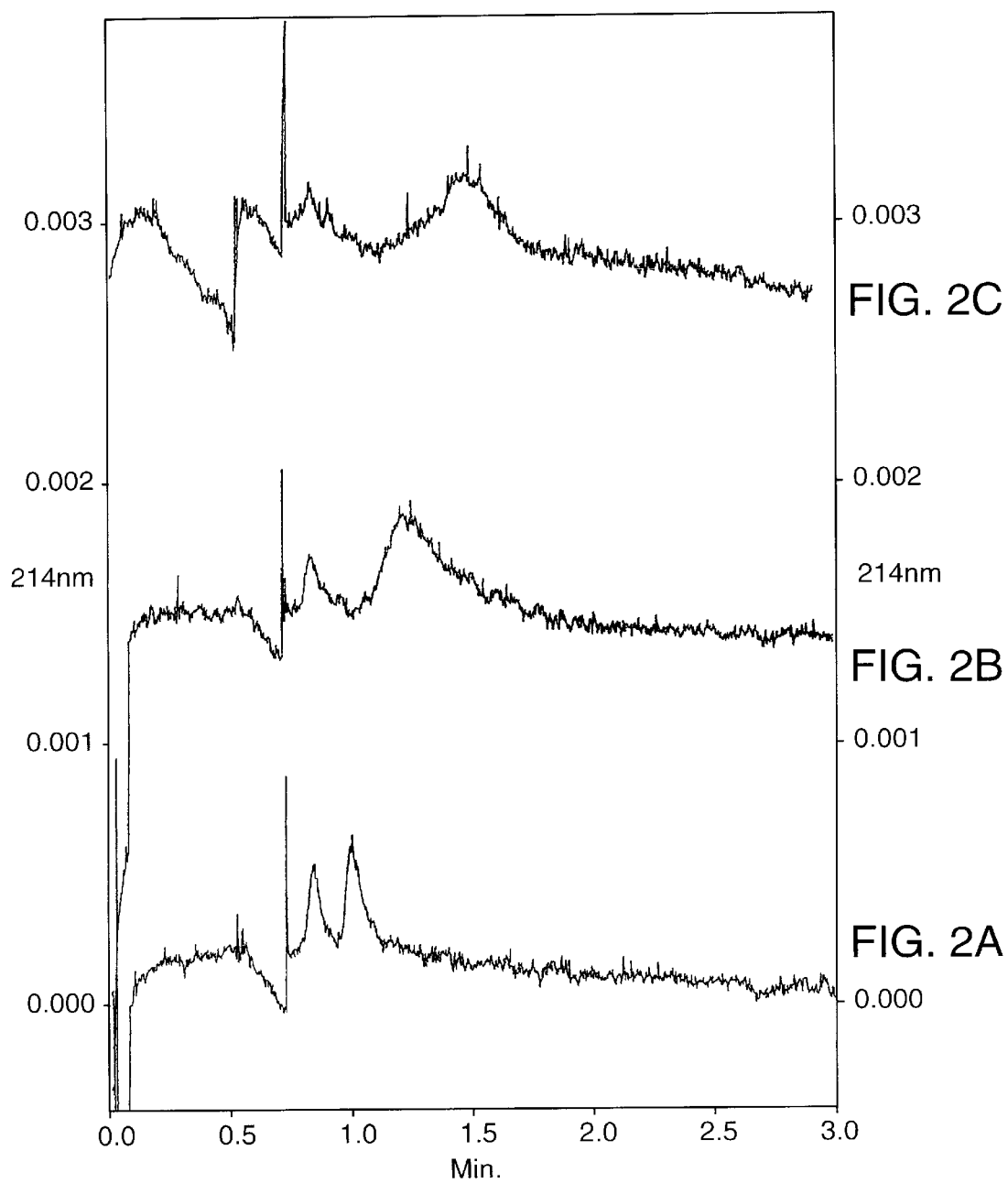
FIG. 2 is an electropherogram depicting characterization and detection of a three-membered complex using UV absorbance.

Ultrafast Electrosenaration Assays Practiced in Accordance with the Instant Invention (a) Once formed, characterization and detection of three-membered complex was accomplished using UW absorbance and a coated column, for example, at pH 4.40. As illustrated in FIG. 2a, two peaks were obtained from the conjugation mixture, one contained excess poly-Glu and the other contained conjugated F(ab')-poly-Glu. As expected, the conjugated fragment had a lower mobility than the free poly-Glu. Under these particular 10 conditions, excess unconjugated F(ab') did not elute, as only negatively charged species migrated in this polarity. Upon addition of the analyte hCG to the reaction mixture containing second binding partner, the conjugated F(ab')-poly-Glu-shifted to a lower mobility and a broader peak was obtained (See FIG. 2b). Addition of the first binding partner, i.e., matched F(ab') that is fluorescently labeled, resulted in further shifts to a lower mobility (FIG. 2c), and complex formation was obtained. The complex migrated as a negatively charged molecule-at pH 4.40 in about 1.5 minutes.

Figure 3:
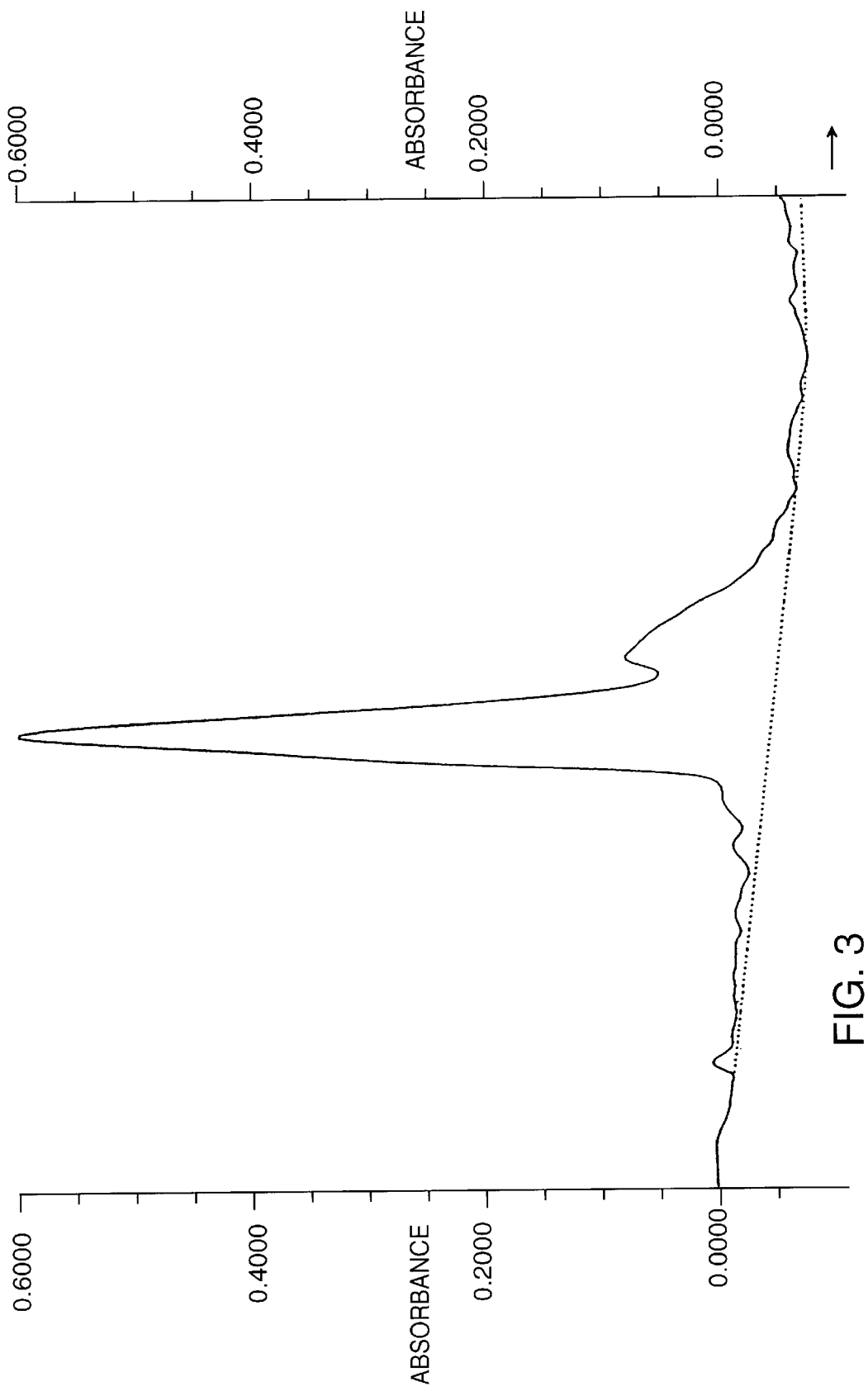
FIG. 3 is an electropherogram depicting characterization and detection of a three-membered complex using fluorescence.

(b) In another experiment using fluorescence detection, complex formation was further confirmed using a coated capillary column with no electro-osmotic flow and a background electrolyte at pH 4.40 (FIG. 3). Under these conditions, the complex containing a fluorescently labeled antibody, a matched F(ab') fragment conjugated at the hinge region with poly-Glu (molecular weight approximately 36,000), and the analyte hCG migrated as a negatively charged species under 1 minute. Experimental parameters have been observed whereby only negatively charged species at pH 4.40 that carry a fluorescent label are detected. Thus a fluorescent signal only resulted from complex formation since the fluorescently labeled unbound antibody was positively charged at this pH. Peak shape and migration time were reproducible.

(c) In certain embodiments of the instant invention, different electrophoretic conditions, including untreated fused silica capillaries, have been used. These conditions served two purposes: first, solute-wall interaction was decreased without having to resort to extreme pH's; and second, the electro-osmotic flow was decreased so that the complex migrated against the flow very rapidly. A currently preferred media is a high concentration of a biological buffer (amino caproic acid/acetic acid, 0.1M) in combination with 0.1% methyl cellulose. This produced good peak shape coupled with good migration time reproducibility.

Figure 4A:
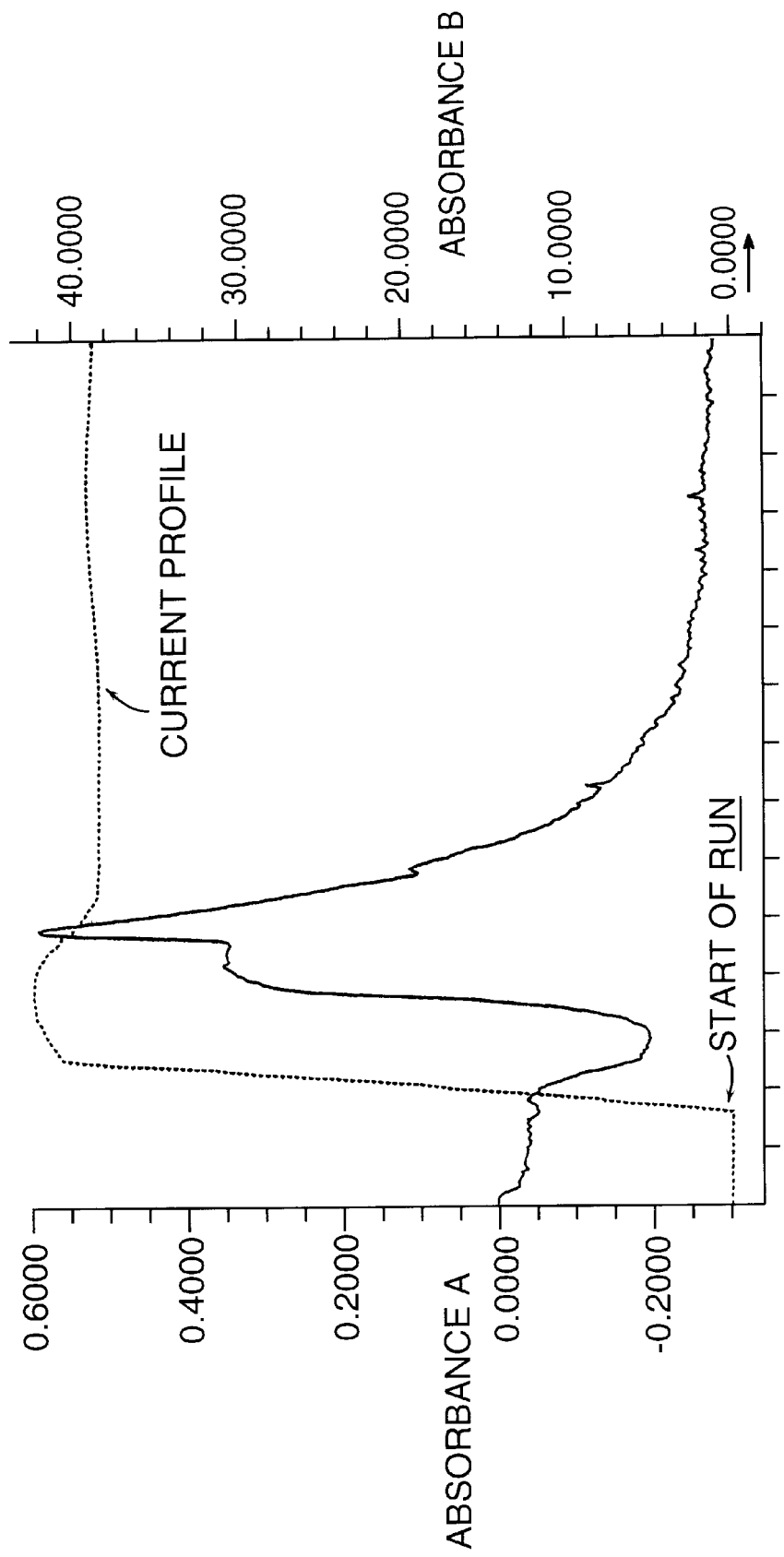
FIG. 4 is an electropherogram conducted using an untreated fused-silica capillary.

Using the above-described experimental conditions, complex was detected within 45 seconds of the injection migrating against the electro-osmotic flow (FIG. 4a). Such conditions were particularly suitable for use with the above-described microfabricated electroseparation apparatus.

Figure 4B:
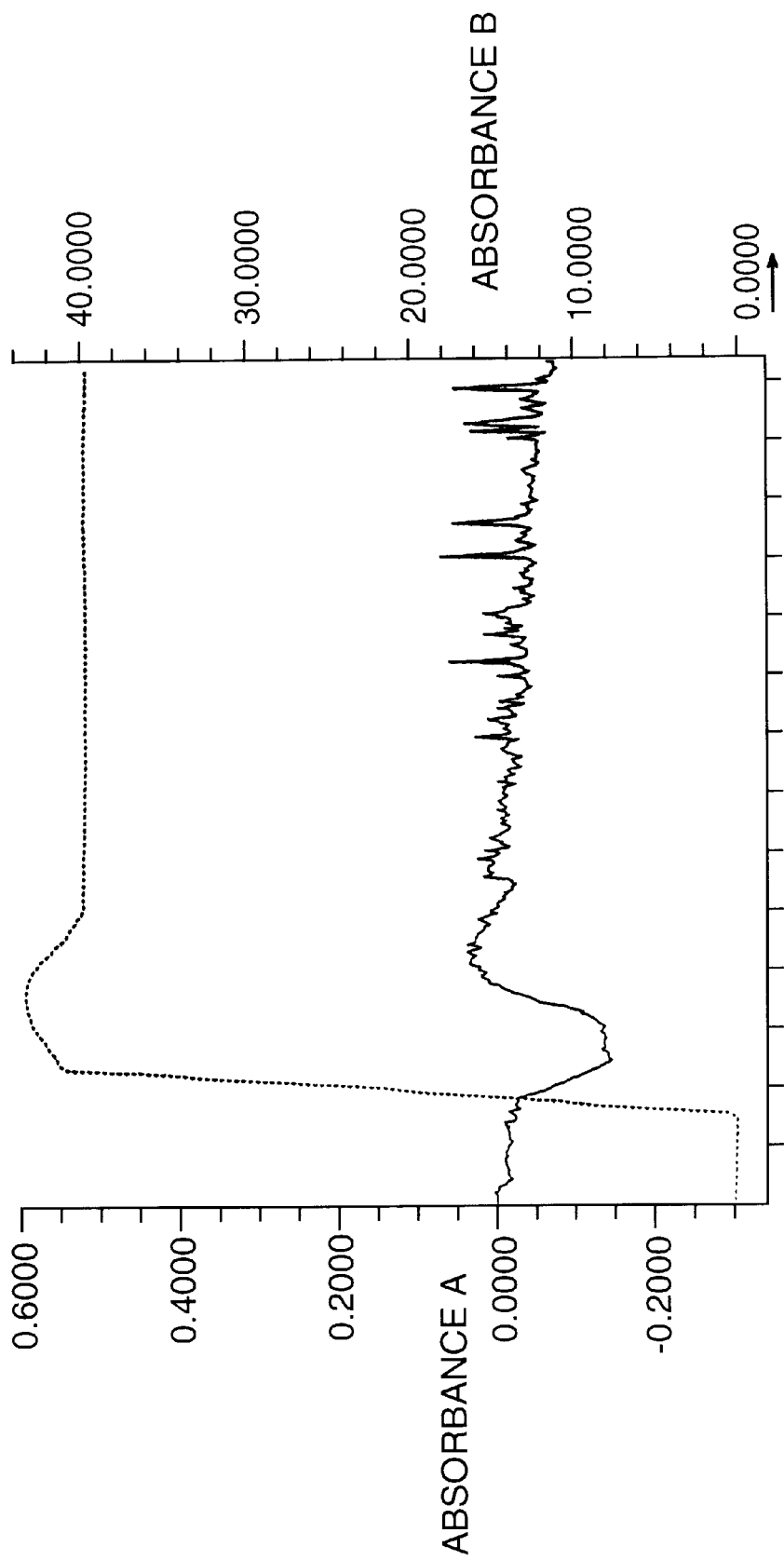
Figure 5A:
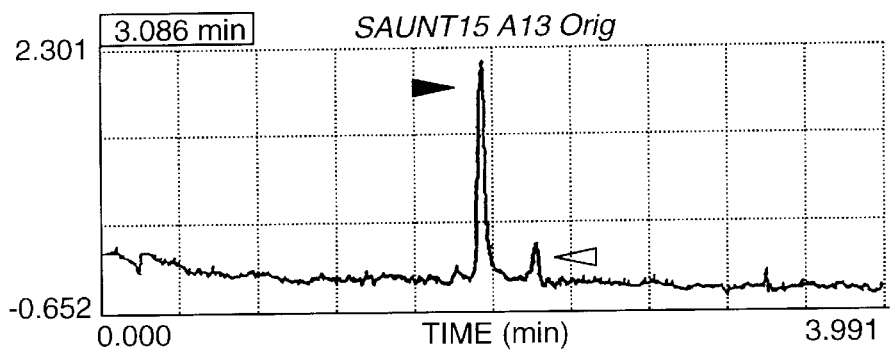
FIG. 5 is an electropherogram depicting the migration behavior of highly negatively charged three-membered complex using a poly-Glu charge-modified second binding partner.
Figure 5B:
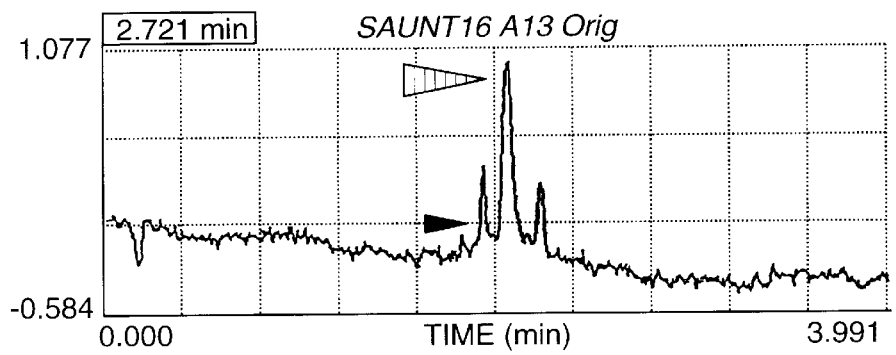
Figure 5C:
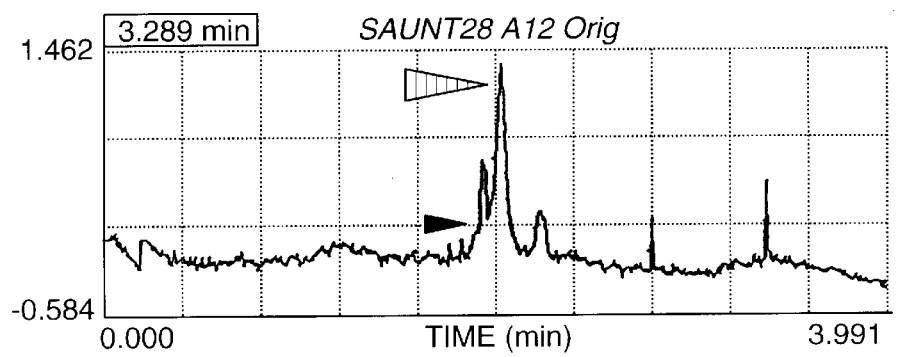
Figure 5D:
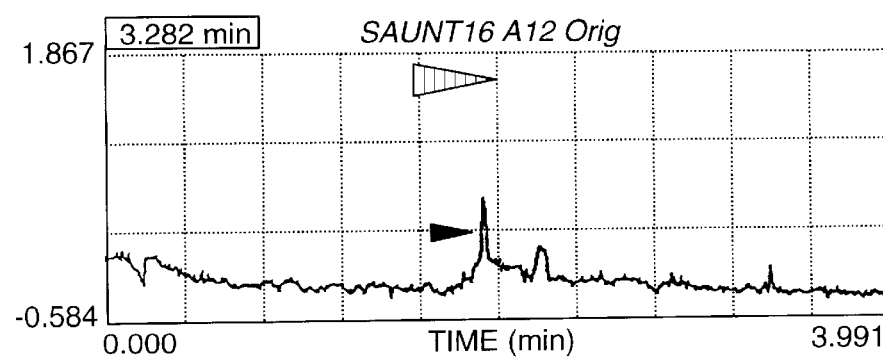

To further confirm complex formation, an experiment was performed in the absence of hCG. In this type of-experiment, the labeled antibody and the F(ab')-poly-Glu were incubated in the absence of hCG under otherwise identical conditions to those described for FIG. 4a. As expected, no complex-containing peak was detected in the absence of the analyte (see FIG. 4b).

Experiments using frontal electrophoresis under the same experimental conditions, i.e., untreated capillary, were also conducted. In this case, the buffer reservoir at the ground end was replaced with the analyte and electrophoresis proceeded without sample injection. Since the complex was the only molecule with sufficient electrophoretic mobility to migrate, a plateau was eventually established.

(d) As described earlier, electroseparation performed using certain embodiments of the present invention results in the three-membered complex and unbound first binding partner migrating in opposite directions. In such extreme circumstances, separation of these species is substantially completely achieved.

This is illustrated in FIG. 5: Panel A is an electropherogram of rhodamine-labeled anti-hCG antibody (solid arrow); the minor species (open arrow) depicted in Panel A is the internal standard, rhodamine. (Impurities also migrate similarly to that depicted by the open arrow.) The medium used was 25 mM phosphate buffer, pH 6.75, containing 1 M AccuPure™ (Waters Corp., Milford, Mass.). Panel B depicts addition of the analyte hCG to the rhodamine-labeled anti-hCG antibody preparation. In panel B, the hatched arrow identifies the antigen-antibody duplex which is somewhat distinguishable from the labeled antibody alone (solid arrow). Panel C depicts addition of unconjugated poly-Glu ($5 \times 10^{-6}$ M, 36,000 molecular weight) which does not notably affect the migration of either unbound labeled antibody or the antigen-antibody duplex. In contrast, as clearly depicted in Panel D, addition of a second antibody now conjugated with the above-described poly-Glu and thereby charge-modified, results in the virtual disappearance of antigen-antibody duplex (see hatched arrow, Panel D).

The duplex peak representing hCG bound to rhodamine-labeled anti-hCG antibody (Panel B) was converted to a three-membered complex upon the addition of the poly-Glu-conjugated second antibody. This three-membered complex then acquired a sufficient negative charge from the second antibody such that it did not elute under these experimental conditions. That is, under these conditions, the other species were swept towards the negative electrode by virtue of strong electro-osmotic flow while the highly negatively charged complex migrated so slowly that it was not detected within a time-frame comparable to the detection of the other labeled species in the electroseparation capillary. In other similar experiments, the complex migrated in the direction opposite to the electro-osmotic flow and was the only species detected. In either instance, virtually complete separation of the three-membered complex from unbound labeled binding partner was achieved.

These observations illustrate that conditions of separation can be manipulated by the skilled artisan so that any desired degree of separation can be accomplished. In general, a large degree of separation such as shown in FIG. 5, Panel D, is desirable for applications where there is significant heterogeneity in the antigen, where a fast separation is desired or where enzyme amplification will be used and therefore good separation of product formed by the complex from that formed by the free labeled binding partner is necessary. For other applications, less separation may be more desirable.

The electroseparation conditions used for the experiments depicted in FIG. 5 would also be well suited for analysis using free-flow electrophoresis. In free-flow electrophoresis, a hydraulically pumped flow of separation medium in which a stream of sample fluid is entrained is subjected to an electric field which is orthogonal to the direction of flow. The electric field causes the entrained sample stream to split into separate streams of sample components based on electrophoretic mobility. These streams can be detected or collected for analysis. The separation is typically not of very high resolution but the method can process larger volumes of sample than can generally be used in capillary electrophoresis. The results depicted in FIG. 5, Panel D, show a situation where the complex and the labeled antibody have very different migration behavior in the electric field. In free-flow electrophoresis, using the same reagents and separation medium, the complex and the labeled antibody would rapidly diverge into separate streams making detection of the complex straightforward.

Figure 6A:
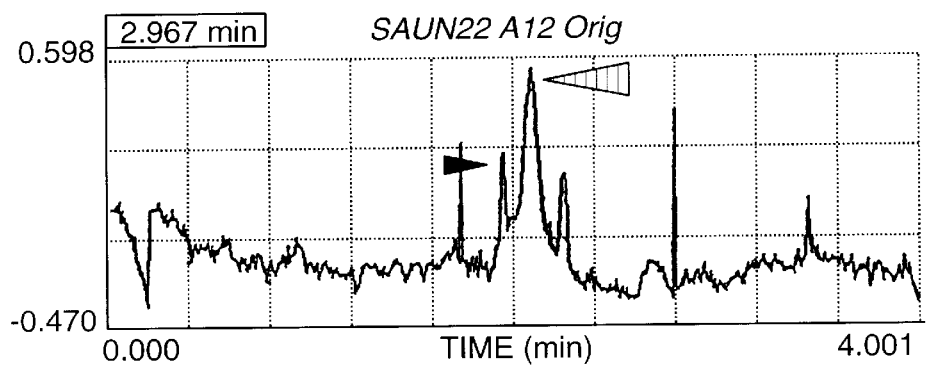
FIG. 6 is an electropherogram depicting the role of charge-modified second binding partner in the migration of three-membered complex.
Figure 6B:
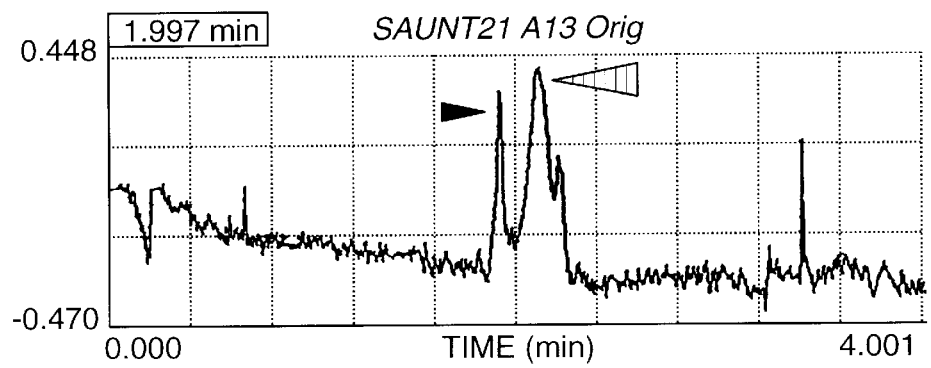

(e) FIG. 6 is an electropherogram obtained using a multi-site charge-modified second binding partner. Electroseparation was conducted using an untreated fused-silica capillary and 25 mM phosphate, pH 6.75, containing 1 M AccuPure™ (Waters Corp., Milford, Mass.). Panel B depicts the migration of three-membered complex (hatched arrow) containing hCG, rhodamine-labeled first antibody, and succinilated charge-modified second antibody. The complex is clearly and distinctly separated from unbound rhodamine-labeled antibody (solid arrow). When comparing Panel B with Panel A, the dependence of this separation upon the charge-modified second antibody becomes evident. In Panel A, the hatched arrow also indicates three-membered complex, however, this particular complex contains hCG, labeled first antibody, and unmodified, uncharged second antibody. Thus, the fact that charge modifications to the second binding partner effectuate the separation of species by causing a shift towards a more negative region in the capillary is clearly illustrated by Panels A and B of FIG. 6.

Figure 7A:
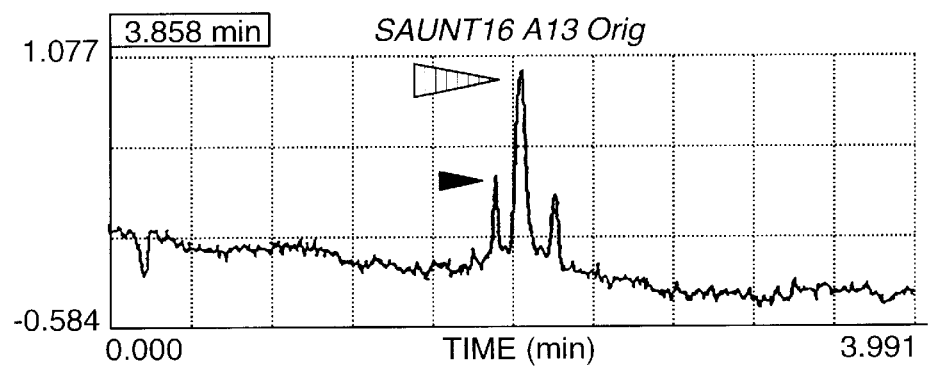
FIG. 7 is an electropherogram depicting the use of multisite charge-modified second binding partner in electroseparation practiced in accordance with the present invention.
Figure 7B:
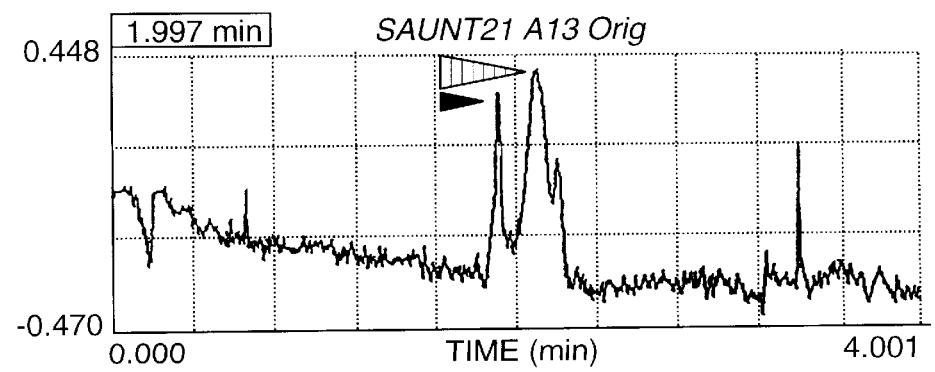

FIG. 7 is an electropherogram also obtained using a multi-site charge-modified second binding partner. The experimental conditions were as described for FIG. 6. Panel A depicts the migration of rhodamine-labeled anti-hCG antibody (solid arrow) and a duplex of rhodamine-labeled antibody and hCG (hatched arrow). The internal standard rhodamine is indicated by the open arrow. Panel B depicts the addition of succinilated charge-modified anti-hCG second antibody. Now the hatched arrow indicates a three-membered complex and a clear shift towards higher negative mobility relative to Panel A. Now the separation of labeled species is enhanced and interference by labeled antibody alone (solid arrow) markedly reduced.

(f) Generally speaking, qualitatively detecting the presence or absence of an analyte according to the instant invention requires: identifying the matched binding partners, e.g., antibodies, for a particular analyte; and thereafter conjugating the first antibody with a detectable moiety, while conjugating the second antibody such that it is modified to be highly charged. The three-membered complex formed upon incubation with analyte carries both the fluorescent moiety and the charge, and thus is easily separated from excess fluorescent antibody.

In an exemplary experiment using single-site charge modifications, matched anti-hCG antibodies were first digested with pepsin, followed by reductive cleavage of the hinge region using 2-mercaptoethylamine. This treatment generated Fab' fragments with free thiol groups at the hinge region. One Fab' was labeled with tetramethylrhodamine-5-iodoacetamide that reacts only with free thiols at.neutral pH. The other Fab' was treated as follows: the heterogeneous bifunctional cross linker N-succinimidyl-6-maleimidocaproate was first reacted in a 100 molar excess with the terminal amino group of poly-Glu [molecular weight approximately 36,000; mean d.p. of 240]. Excess reagent was removed using a Sephadex G-25 gel filtration column. The maleimido group of the activated poly-Glu was then selectively reacted with the thiol groups of the Fab' at pH 6.0.

Upon combining (a) the above-described first binding partner, i.e., fluorescently labeled Fab', (b) second binding partner, i.e., the poly-Glu conjugated Fab', and, (c) the analyte hCG, complex was qualitatively detected using both UV absorbance and fluorescence detection. Using a coated capillary with no electro-osmotic flow, the complex was detected as a negatively charged species at pH 4.4. Insofar as using untreated fused silica capillaries is concerned, a high concentration of biological buffer (amino caproic acid/ acetic acid, 0.1 M) in combination with 0.1% methyl cellulose gave a reasonable peak shape with good migration time reproducibility. Qualitatively, the complex was detected within 45 seconds of injection migrating against the electro-osmotic flow.

(g) Quantitation of the analyte hCG in a biological sample such as urine can be performed by measuring the formation of the complex of hCG, first binding partner and second binding partner, detected in the above-described electroseparation analysis. For example, the assay can be performed by combining 10 $\mu$L of the urine sample, 10 $\mu$L of $3\times10^{-6}$ M rhodamine-labeled Fab' and 10 $\mu$L of $3\times10^{-6}$ M poly-Glu conjugated Fab'. The mixture is incubated at 37° C. for 5 minutes. Following incubation, 10 nl of the sample mixture is injected into a polyacrylamide coated capillary containing 0.1 M $\epsilon$-amino caproic acid and 0.1% methyl cellulose, adjusted to pH 4.4 with acetic acid. The separation is performed at 30 kV applied potential and the complex peak is detected by laser fluorescence detection using the 514 nm argon ion laser for excitation and selecting emission wavelengths around 590 nm with a bandpass filter having a 20 nm bandpass. The peak is quantitated by peak area determination as is well-known in the art. The amount of hCG present in the urine sample is determined by comparing the peak area of the complex to a calibration curve previously obtained by running known standards of hCG prepared in urine devoid of hCG. It is expected that quantitative analysis using electroseparation materials and methods as disclosed herein will permit detection of hCG at a sensitivity level of at least about $10^{-10}$ M or approximately about 49 mIU/ml.

As discussed earlier, enzymes are suitable detection moieties for use with the materials and methods of the instant invention. It is expected that quantitative electroseparation assays using the enzyme, alkaline phosphatase, conjugated to a first binding partner using art-recognized techniques will permit measurement of hCG, for example, with a sensitivity of at least about $10^{-12}$ M or approximately about 0.49 mIU/ml. Enzyme assays which employ enzyme amplification for signal enhancement are recognized by the skilled artisan as being preferred for certain analytes such as thyroid stimulating hormone. Enzyme conjugation techniques and enzyme amplification protocols are well-known in the art, and selection of suitable enzyme-substrate reagents for use in the instant invention is well within the skill of the ordinary practitioner using routine experimentation.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An electroseparation apparatus for the detection of an analyte comprising:
   (a) electroseparation channel comprising
      (i) an electrically-conductive medium;
      (ii) an injection zone; and,
      disposed within said injection zone
         (1) a first binding partner which binds to a first binding site on said analyte, said first binding partner further comprising a detection moiety; and,
         (2) a second binding partner which binds to a second binding site on said analyte, said second binding partner further comprising a charge-modifying moiety,
      wherein said second binding site is distinct from said first binding site such that the analyte, the first binding partner, and the second binding partner form a three-membered complex;
   (b) source of voltage for imposing an electric potential across said channel; and
      means for detecting said analyte.

2. The apparatus of claim 1 wherein activation of said electric potential results in said three-membered complex and unbound first binding partner resolving into two opposite moving zones, one zone containing said three-membered complex and another zone containing said unbound first binding partner, resulting in separation of said three-membered complex from said unbound first binding partner sufficient to permit detection of said analyte.

3. The apparatus of claim 1 wherein said electroseparation channel comprises a solid substrate microfabricated to define at least one channel.

4. The apparatus of claim 3 wherein said electroseparation channel comprises a linear passage through said substrate.

5. The apparatus of claim 3 wherein said solid substrate comprises an organic polymer.

6. The apparatus of claim 3 wherein at least a portion of said channel has a width between about 0.1 $\mu$m and about 1000 $\mu$m and a depth between about 0.1 $\mu$m and about 1000 $\mu$m.

7. The apparatus of claim 6 wherein the channel width is about 10 $\mu$m to about 1000 $\mu$m.

8. The apparatus of claim 6 wherein the channel depth is about 5 μm to about 100 μm.

9. The apparatus of claim 1 wherein said electroseparation channel comprises a capillary.

10. The apparatus of claim 9 wherein the capillary is less than about 500 μm in diameter.

11. The apparatus of claim 10 wherein the capillary further comprises an inner wall with a charge.

12. The apparatus of claim 10 wherein the capillary further comprises an inner wall with a covalent modification.

13. The apparatus of claim 10 wherein the capillary further comprises an inner wall dynamically modified by the introduction of buffer additives thereon.

14. The apparatus of claim 1 wherein the electrophoretic mobility of an three-membered complex is opposite electroosmotic flow, thereby causing said complex to be injected electrokinetically.

15. The apparatus of claim 1 wherein the electrophoretic mobility of said three-membered complex differs from that of said unbound first binding partner.

16. The apparatus of claim 1 wherein the means for detecting said analyte further comprises means for detecting said three-membered complex which is indicative of the presence of analyte in the sample.

17. The apparatus of claim 1 further comprising a means for quantitatively determining the amount of said analyte in said sample.

18. The apparatus of claim 17 wherein the means for determining the amount of said analyte further comprises means for determining quantitatively the formation of said three-membered complex which is indicative of the concentration of analyte in said sample.

19. An electroseparation apparatus for the detection of an analyte in a sample comprising:
   (a) electroseparation channel;
   (b) means for disposing within said channel a mixture comprising:
      (ii) a first binding partner which binds to a first binding site on said analyte, said first binding partner comprising a detectable moiety;
      (ii) a second binding partner which binds to a second binding site on said analyte, said second binding partner comprising a charge-modifying moiety;
      (iii) a three-membered complex, said complex comprising said analyte, said first binding partner, and said second binding partner; and,
   (c) source of voltage for imposing an electrical potential across said channel; and
   means for detecting said analyte.

20. A kit for electroseparation analysis of an analyte in a sample comprising:
   (a) an electroseparation apparatus comprising a channel;
   (b) a detectable moiety for attachment to a first binding moiety, said first binding moiety competent to bind to a first binding site on an analyte in a sample; and,
   (c) a charge-modifying moiety for attachment to a second binding moiety, said second binding moiety competent to bind to a second binding site on said analyte in said sample.

21. The kit of claim 20 further comprising attachment reagents with which said detectable moiety and said charge-modifying moiety can be attached to said first and second binding moieties, respectively, to form a first binding partner and a second binding partner, respectively, said first binding partner and said second binding partner being competent to bind to said analyte, if present in said sample, thereby forming a three-membered complex which exhibits an electrophoretic mobility different from that of unbound first binding partner during electroseparation analysis.

22. The kit of claim 20 wherein said channel comprises a capillary having a diameter of less than about 500 μm.

23. A kit for electroseparation analysis of an analyte in a sample comprising:
   (a) a first binding partner which binds to a first binding site on an analyte, said first binding partner comprising a detectable moiety; and,
   (b) a second binding partner which binds to a second binding site on said analyte, said second binding partner comprising a charge-modifying moiety
      such that said first and second binding partners form a three-membered complex with said analyte, if present, thereby permitting detection of complexed analyte by electroseparation.

* * * * *